(12) United States Patent
Liu

(10) Patent No.: US 11,517,261 B2
(45) Date of Patent: Dec. 6, 2022

(54) METHOD AND DEVICE FOR DETERMINING INNER AND OUTER SIDES OF LIMBS

(71) Applicant: BEIJING ZHIGU TECH CO., LTD., Beijing (CN)

(72) Inventor: Hao Liu, Beijing (CN)

(73) Assignee: BEIJING ZHIGU TECH CO., LTD., Beijing (CN)

( * ) Notice: Subject to any disclaimer, the term of this patent is extended or adjusted under 35 U.S.C. 154(b) by 970 days.

(21) Appl. No.: 15/511,197

(22) PCT Filed: Sep. 10, 2015

(86) PCT No.: PCT/CN2015/089303
§ 371 (c)(1),
(2) Date: Mar. 14, 2017

(87) PCT Pub. No.: WO2016/041460
PCT Pub. Date: Mar. 24, 2016

(65) Prior Publication Data
US 2017/0258399 A1     Sep. 14, 2017

(30) Foreign Application Priority Data

Sep. 15, 2014  (CN) .......................... 201410468258.4
Sep. 15, 2014  (CN) .......................... 201410468266.9
(Continued)

(51) Int. Cl.
*A61B 5/00*   (2006.01)
*A61B 5/01*   (2006.01)
(Continued)

(52) U.S. Cl.
CPC ................ *A61B 5/681* (2013.01); *A61B 5/01* (2013.01); *A61B 5/02416* (2013.01);
(Continued)

(58) Field of Classification Search
CPC ....... A61B 5/681; A61B 5/01; A61B 5/02416; A61B 5/0531; A61B 5/14539;
(Continued)

(56) References Cited

U.S. PATENT DOCUMENTS

| 8,676,313 B2 | 3/2014 | Volpe et al. |
| 2011/0071419 A1* | 3/2011 | Liu ...................... A61B 5/0053 600/547 |

(Continued)

FOREIGN PATENT DOCUMENTS

| CA | 2847645 A1 | 6/2014 |
| CN | 103164153 A | 6/2013 |

(Continued)

OTHER PUBLICATIONS

International Search Report and Written Opinion for Application No. PCT/CN2015/089303, dated Dec. 3, 2015, 10 pages.

(Continued)

*Primary Examiner* — Rex R Holmes
*Assistant Examiner* — Sana Sahand

(57) ABSTRACT

The present application provides a method and device for determining inner and outer sides of limbs, and relates to the field of wearable devices. The method comprises: acquiring first somatosensory information of a first side of a limb of a user, the first side being an inner side or an outer side of the limb; and determining whether the first side is the inner side of the limb according to the first somatosensory information and reference information. The method and device facilitate a device that the user wears to perform automatic setting according to an identification result, thereby enhancing user experience.

95 Claims, 23 Drawing Sheets

(30) Foreign Application Priority Data

| | | |
|---|---|---|
| Sep. 15, 2014 | (CN) | 201410468268.8 |
| Sep. 15, 2014 | (CN) | 201410468272.4 |
| Sep. 15, 2014 | (CN) | 201410468521.X |
| Sep. 15, 2014 | (CN) | 201410468701.8 |
| Sep. 15, 2014 | (CN) | 201410468705.6 |
| Dec. 17, 2014 | (CN) | 201410788423.4 |

(51) Int. Cl.
*A61B 5/0531* (2021.01)
*A61B 5/1455* (2006.01)
*A61B 5/024* (2006.01)
*A61B 5/145* (2006.01)

(52) U.S. Cl.
CPC ........ *A61B 5/0531* (2013.01); *A61B 5/14539* (2013.01); *A61B 5/14542* (2013.01); *A61B 5/14551* (2013.01); *A61B 5/4872* (2013.01); *A61B 5/7246* (2013.01); *A61B 2562/029* (2013.01)

(58) Field of Classification Search
CPC ............ A61B 5/14542; A61B 5/14551; A61B 5/4872; A61B 5/7246; A61B 2562/029
See application file for complete search history.

(56) References Cited

U.S. PATENT DOCUMENTS

| | | | |
|---|---|---|---|
| 2011/0245622 A1* | 10/2011 | McKenna | G06F 19/00 600/300 |
| 2014/0081179 A1 | 3/2014 | Moore-Ede | |
| 2014/0094675 A1* | 4/2014 | Luna | A61B 5/0245 600/386 |
| 2014/0099614 A1 | 4/2014 | Hu et al. | |
| 2014/0366123 A1* | 12/2014 | DiBona | G06F 21/6218 726/16 |
| 2015/0031964 A1* | 1/2015 | Bly | A61B 5/681 600/301 |
| 2015/0054728 A1* | 2/2015 | Choi | G06F 3/017 345/156 |

FOREIGN PATENT DOCUMENTS

| | | |
|---|---|---|
| CN | 103393260 A | 11/2013 |
| CN | 203299558 U | 11/2013 |
| CN | 103677265 A | 3/2014 |
| CN | 103941873 A | 7/2014 |
| CN | 104161512 A | 11/2014 |
| CN | 104199543 A | 12/2014 |
| CN | 104224118 A | 12/2014 |
| CN | 104224119 A | 12/2014 |
| CN | 104224120 A | 12/2014 |
| CN | 104224121 A | 12/2014 |
| CN | 104224122 A | 12/2014 |
| CN | 104224123 A | 12/2014 |
| CN | 104224124 A | 12/2014 |
| CN | 104463131 A | 3/2015 |
| JP | 2006296700 A | 11/2006 |

OTHER PUBLICATIONS

Sanxin Yu, Chapter 2—Basic Principals, Functional Diagnostics, Mar. 1, 1997, p. 204 (with English Translation), 4 pages.

Office Action for Chinese Application No. 201410468266.9, dated Nov. 15, 2016, (with English Translation), 12 pages.

Office Action for Chinese Application No. 201410788423.4, dated Mar. 30, 2017, (with English Translation), 13 pages.

* cited by examiner

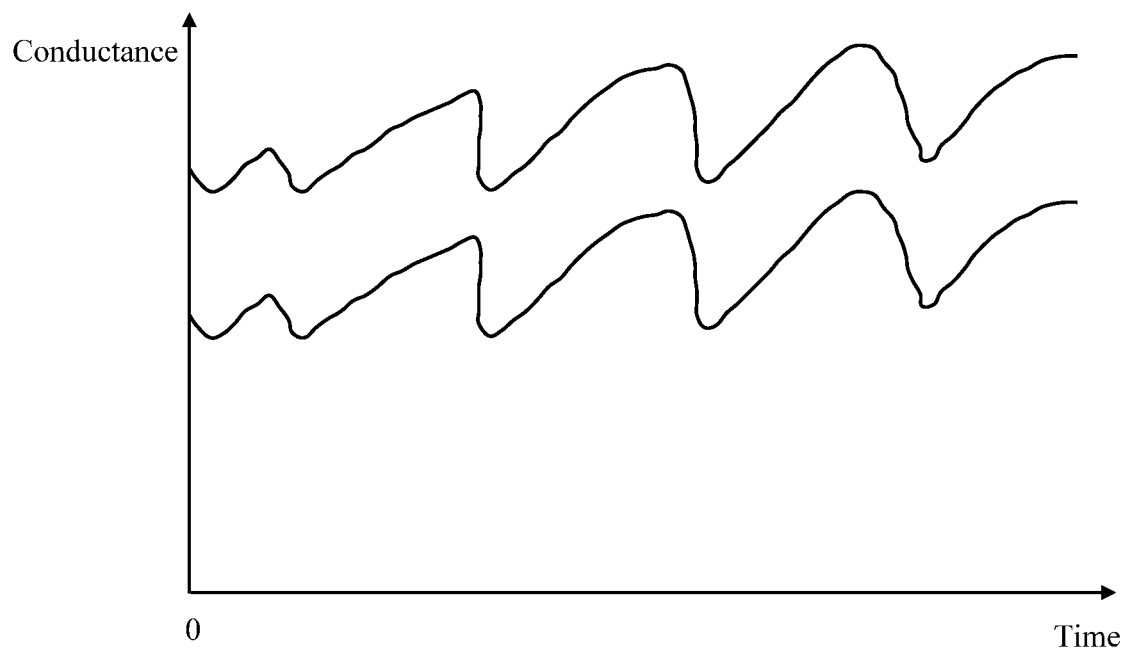

FIG. 3

| Determining that the first side is the inner side of the limb in response to determining that the average value of the first skin conductive information is greater than the average value of the second skin conductive information | S141a |

↓

| Determining that the first side is not the inner side of the limb in response to determining that the average value of the first skin conductive information is less than the average value of the second skin conductive information | S142a |

FIG. 4

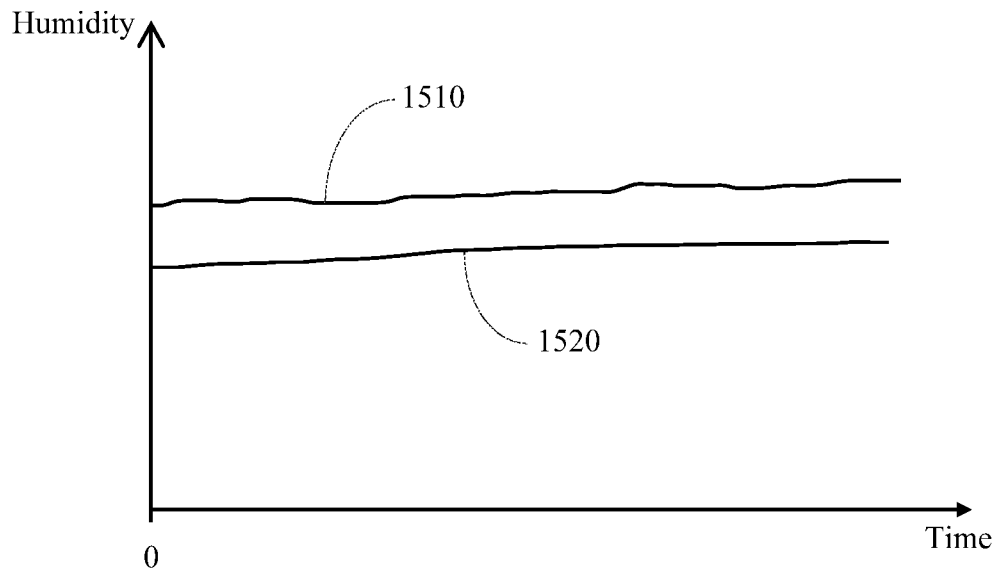

FIG. 15

| Determining that the first side is the inner side of the limb in response to determining that the average value of the first humidity information is greater than the average value of the second humidity information | S141e |
|---|---|
| Determining that the first side is not the inner side of the limb in response to determining that the average value of the first humidity information is less than the average value of the second humidity information | S142e |

METHOD AND DEVICE FOR DETERMINING INNER AND OUTER SIDES OF LIMBS

RELATED APPLICATION

This application is a national phase application of International Application No. PCT/CN2015/089303, filed on Sep. 10, 2015, which claims the benefit of priority to Chinese Patent Application No. 201410788423.4, which was filed on Dec. 17, 2014 and entitled "Method and Device for Determining Inner and Outer Sides of Limbs," and Chinese Patent Applications No. 201410468272.4, No. 201410468268.8, No. 201410468701.8, No. 201410468266.9, No. 201410468258.4, No. 201410468521.X, No. 201410468705.6, all of which were filed on Sep. 15, 2014 and entitled "Method and Device for Determining Inner and Outer Sides of Limbs". All of the aforementioned applications are incorporated by reference herein in their entirety.

TECHNICAL FIELD

The present application relates to the field of wearable devices, and in particular, to a method and device for determining inner and outer sides of limbs.

BACKGROUND

In recent years, with the development of wearable devices, smart wristbands, smart bracelets, smart glasses and the like have gradually entered into people's life, thus greatly enriching and facilitating people's life.

For example, a somatosensory sensor configured on a smart watch may continuously monitor the somatosensory data of a user, such as body temperature, heart rate and blood sugar, so as to provide the user with health care services. The somatosensory sensor is either embedded in the back of the dial, or embedded in the inside of the strap, according to the measurement principle. While such a somatosensory sensor can accurately measure somatosensory data of the user by closely clinging to the inside of the wrist of the user, the user must wear a smart watch in a fixed manner, thus bringing about inconvenience to the user. For example, if the somatosensory sensor is embedded in the inside of the strap, the user must wear the dial of the smart watch at the outside of the wrist, which will bring about inconvenience to users who are accustomed to wearing the dial at the inside of the wrist.

SUMMARY

An objective of the present application is to provide a method and device for determining inner and outer sides of limbs.

In a first aspect, an embodiment of the present application provides a method for determining inner and outer sides of limbs. The method comprises:

acquiring first somatosensory information of a first side of a limb of a user, the first side being an inner side or an outer side of the limb; and determining whether the first side is the inner side of the limb according to the first somatosensory information and reference information.

In another aspect, an embodiment of provides a device for determining inner and outer sides of limbs. The device comprises:

a first acquisition module, configured to acquire first somatosensory information of a first side of a limb of a user, the first side being an inner side or an outer side of the limb; and an identification module, configured to identify whether the first side is the inner side of the limb according to the first somatosensory information and reference information.

According to the method and device for determining inner and outer sides of limbs in the embodiments of the present application, first somatosensory information of a first side of a limb of a user is acquired. It is then determined, based on the first somatosensory information and reference information, whether the first side is the inner side of the limb. Based on the determination, automatic setting can be performed on a device worn by the user, thereby user experience can be enhanced.

BRIEF DESCRIPTION OF THE DRAWINGS

FIG. 3 is a schematic diagram of comparison of skin conductive information on inner and outer sides of a wrist according to an embodiment of the present application;

FIG. 4 is a flowchart of part of S140 of FIG. 1 according to an embodiment of the present application;

FIG. 15 is a schematic diagram of comparison of humidity information on inner and outer sides of a wrist in some embodiments of the present application;

FIG. 16 is a flowchart of part of step S140 of FIG. 1 according to an embodiment of the present application;

DETAILED DESCRIPTION

Specific implementations of the present disclosure are described in further detail below with reference to the accompanying drawings and embodiments. The following embodiments are intended to describe the present application, but not to limit the scope of the present application.

It should be understood by those skilled in the art that, in the embodiments of the present application, the value of the serial number of each step described below does not mean an execution sequence, and the execution sequence of each step should be determined according to the function and internal logic thereof, and should not be any limitation to the implementation procedure of the embodiments of the present application.

Figure 1:
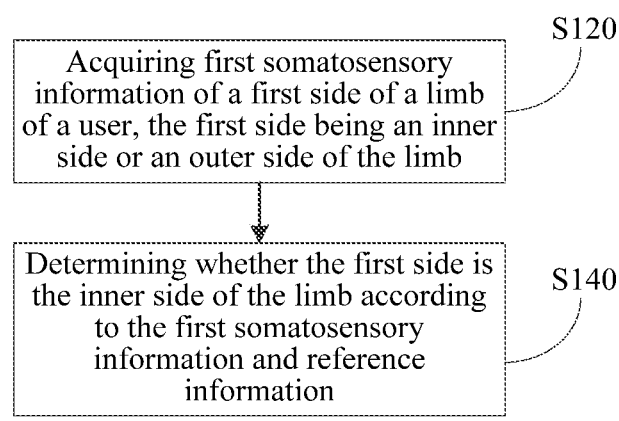
FIG. 1 is a flowchart of the method for determining inner and outer sides of limbs according to an embodiment of the present application.

FIG. 1 is a flowchart of the method for determining inner and outer sides of limbs according to one embodiment of the present application; the method may be implemented on, for example, a device for determining inner and outer sides of limbs. As shown in FIG. 1, the method comprises:

S120: acquiring first somatosensory information of a first side of a limb of a user, the first side being an inner side or an outer side of the limb; and S140: determining whether the first side is the inner side of the limb according to the first somatosensory information and reference information.

According to a method of an embodiment of the present disclosure, first somatosensory information of a first side of a limb of a user is acquired, and then whether the first side is the inner side of the limb is determined according to the first somatosensory information and reference information, so as to provide a method for determining inner and outer sides of limbs, which facilitates a device that the user wears to perform automatic setting according to an identification result, thereby enhancing user experience.

Functions of steps S120 and S140 are described below in detail in combination with specific implementations.

S120: Acquire first somatosensory information of a first side of a limb of a user, the first side being an inner side or an outer side of the limb.

Figure 2:
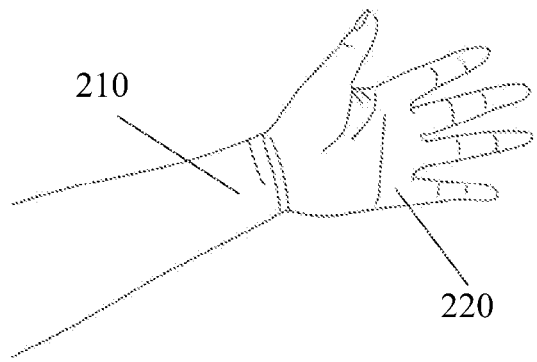
FIG. 2 is a schematic diagram of an inner side of a wrist and an inner side of a palm according to an embodiment of the present application.

The limb may comprise an upper limb and a lower limb of the user. Specifically, the inner side of the limb may be an inner side of a wrist, an inner side of a palm or an inner side of a sole, and correspondingly, the outer side of the limb may be an outer side of the wrist, an outer side of the palm or an outer side of the sole. As shown in FIG. 2, the inner side of the palm can be a palm center 220 and a region corresponding to fingers on one side of the palm center 220 in FIG. 2, and the outer side of the palm can be the back of the hand and a region corresponding to fingers on one side of the back of the hand; the inner side of the wrist can be a first region 210 on the same side with the palm center 220 and located between the palm and a forearm in FIG. 2, the outer side of the wrist can be opposite to the first region 210 and can be a second region on the same side with the back of the hand and located between the palm and the forearm. The inner side of the sole can be a region corresponding to the bottom of a foot, and the outer side of the sole can be a region corresponding to the top of the foot.

The first side can be the inner side or outer side of the wrist, or the inner side or outer side of the palm, or the inner side or outer side of the sole. For the sake of simplicity, description is given below mostly by taking that the first side as the inner side or outer side of the wrist as an example.

The first somatosensory information may be skin conductive information, body temperature information, PH information, PPG information, humidity information, blood oxygen information or fat information of the first side of the limb, etc., which can be acquired through a corresponding somatosensory sensor in contact with the skin of the user. Since typically smart wristbands, smart watches and the like have the sensors, implementation of the method will not increase substantially the hardware costs of the existing wearable devices.

S140: Identify whether the first side is the inner side of the limb according to the first somatosensory information and reference information.

a) The first somatosensory information may include skin conductive information of the first side, which can be first skin conductive information. Step S140 can comprise the following to process first skin conductive information:

S140a: determining whether the first side is the inner side of the limb according to the first skin conductive information and reference information.

The inventor has found in the study that, as the number of sweat glands on the inner side of the limb is typically more than that on the outer side of the limb, and that skin on the outer side of the limb is rougher than that on the inner side of the limb, skin conductance of the inner side of the limb of the user and skin conductance of the outer side of the limb have a statistically significant difference. For example, their variance is less than or equal to 0.05. As shown in FIG. 3, the upper curve indicates a curve of skin conductive information obtained by sampling skin conductive signals on an inner side of a wrist of a user, and the lower curve indicates a curve of skin conductive information obtained by sampling skin conductive signals on an outer side of the wrist of the user. The horizontal axis indicates time, and the unit is in seconds, while the longitudinal axis indicates conductance, and the unit is micro-mho. It can be seen that the two curves have a significant difference, and after analysis, it can be obtained that an average value of skin conductance information of the inner side of the wrist can be significantly greater than an average value of skin conductance information of the outer side of the wrist. Similarly, the inventor has also found that an average value of skin conductance information of the inner side of the palm can be significantly greater than an average value of skin conductance information of the outer side of the palm, and an average value of skin conductance information of the inner side of the sole is significantly greater than an average value of skin conductance information of the outer side of the sole. Therefore, a method of the present disclosure can achieve identification of inner and outer sides of limbs based on the principle.

In some embodiments, the reference information include second skin conductive information acquired at a second side opposite the first side on the limb. For example, two groups of somatosensory sensors can be set, corresponding skin conductive information of the first side and the second side of the limb is acquired at the same time, and the skin conductive information acquired at the second side is used as the reference information.

In some embodiments, in step S140a, whether the first side is the inner side of the limb can be determined by comparing sizes of an average value of the first skin conductive information and an average value of the second skin conductive information; specifically, as shown in FIG. 4, the step may comprise:

S141a: determining that the first side is the inner side of the limb in response to determining that the average value of the first skin conductive information is greater than the average value of the second skin conductive information; and S142a: determining that the first side is not the inner side of the limb in response to determining that the average value of the first skin conductive information is less than the average value of the second skin conductive information.

Figure 5:
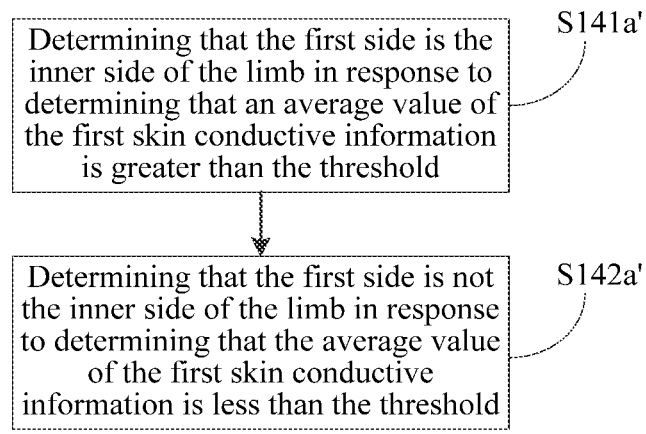
FIG. 5 is a flowchart of part of S140 of FIG. 1 according to an embodiment of the present application.

In some embodiments, the reference information may be a threshold determined according to skin conductive information of the inner side and skin conductive information of the outer side of the limb. Specifically, as shown in FIG. 5, step S140a may comprise:

S141a': determining that the first side is the inner side of the limb in response to determining that an average value of the first skin conductive information is greater than the threshold; and S142a': determining that the first side is not the inner side of the limb in response to determining that the average value of the first skin conductive information is less than the threshold.

For example, skin conductive information of the inner side of the limb and skin conductive information of the outer side of the limb are pre-acquired and analyzed, suppose that an average value of the skin conductive information of the inner side falls within a first interval ($I_{min}$, $I_{max}$) and suppose that an average value of the skin conductive information of the outer side falls within a second interval ($O_{min}$, $O_{max}$), $O_{max} < I_{min}$, it can be determined that the threshold is M, and $O_{max} < M < I_{min}$. That is to say, the threshold M is a value between the first interval and the second interval.

Therefore, if an average value of the first skin conductive information is greater than the threshold M, it can be considered that the average value falls within the first interval, and the first side is the inner side of the limb; if the average value of the first skin conductive information is less than the threshold M, it can be considered that the average value falls within the second interval, and the first side is not the inner side of the limb, that is, is the outer side of the limb.

b) The first somatosensory information may include body temperature information of the first side, that is, first body temperature information. Step S140 can comprise the following to process first body temperature information:

S140b: determining whether the first side is the inner side of the limb according to the first body temperature information and reference information.

Figure 6:
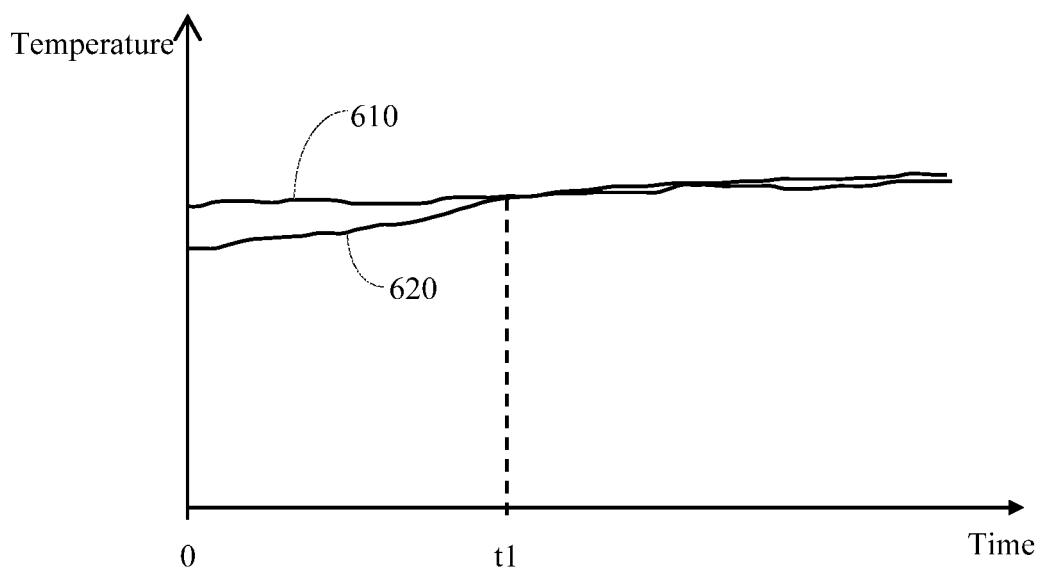
FIG. 6 is a schematic diagram of comparison of temperature information on inner and outer sides of a wrist according to an embodiment of the present application.

The inventor has found in the study that, as the inner side of the limb is much closer to arterial vessels than the inner side of the limb, the body temperature of the inner side of the limb of the user will be higher than that of the outer side of the limb. As shown in FIG. 6, the first curve 610 indicates a curve of body temperature information obtained by sampling body temperature signals of an inner side of a wrist of a user by using a first body temperature sensor, and the second curve 620 indicates a curve of body temperature information obtained by sampling body temperature signals of an outer side of the wrist of the user by using a second body temperature sensor. The horizontal axis indicates time, and the unit is second, while the longitudinal axis indicates temperature, and the unit is degree Celsius; Time 0 can correspond to the time when the user begins to wear the first body temperature sensor and the second body temperature sensor.

It can be seen that the two curves in FIG. 6 have a significant difference before Time $t_1$, and after analysis, it can be obtained that the body temperature of the inner side of the wrist is significantly greater than that of the outer side of the wrist. After the Time $t_1$, the two curves gradually merge, and this is because conduction of heat of a connecting portion which connects the first body temperature sensor and the second body temperature sensor makes body temperatures detected by the two sensors tend to be the same. In another experiment, the connecting portion between the two body temperature sensors is removed, a body temperature curve finally obtained shows that the body temperature of the inner side of the wrist is greater than that of the outer side of the wrist, and a temperature difference thereof is about 0.2° C.

Similarly, the inventor has also found that the body temperature of the inner side of the palm is significantly greater than that of the outer side of the palm, and the body temperature of the inner side of the sole is significantly greater than that of the outer side of the sole. Therefore, a method of the present disclosure can achieve identification of inner and outer sides of limbs based on the principle.

In some embodiments, the reference information include second body temperature information acquired at a second side opposite the first side on the limb. For example, two groups of body temperature sensors can be set, corresponding body temperature information of the first side and the second side of the limb is acquired at the same time, and the body temperature information acquired at the second side is used as the reference information.

Figure 7:
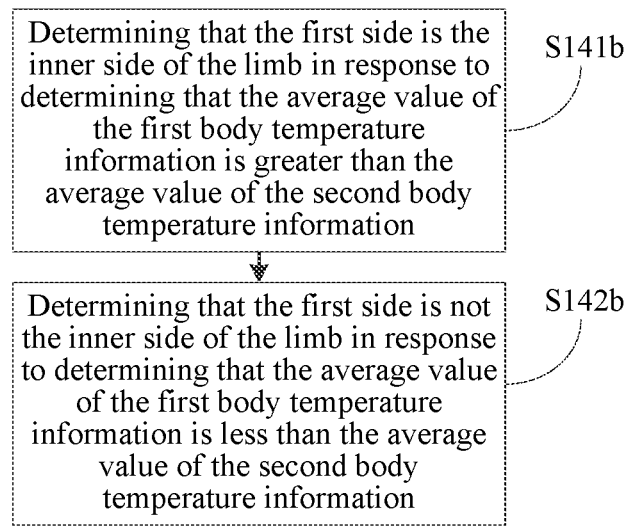
FIG. 7 is a flowchart of part of S140 of FIG. 1 according to an embodiment of the present application.

In some embodiments, in step S140*b*, whether the first side is the inner side of the limb can be determined by comparing sizes of an average value of the first body temperature information and an average value of the second body temperature information. The average value of the first body temperature information can be an average value of temperature values corresponding to a plurality of sampling points in the first body temperature information, and similarly, an average value of the second body temperature information can be an average value of temperature values corresponding to a plurality of sampling points in the second body temperature information. By use of the average value, wrong identification caused by a sampling error occurring in a single sampling point can be avoided, thereby improving identification accuracy. Specifically, referring to FIG. 7, step S140*b* may comprise:

S141*b*: determining that the first side is the inner side of the limb in response to determining that the average value of the first body temperature information is greater than the average value of the second body temperature information; and S142*b*: determining that the first side is not the inner side of the limb in response to determining that the average value of the first body temperature information is less than the average value of the second body temperature information.

Figure 8:
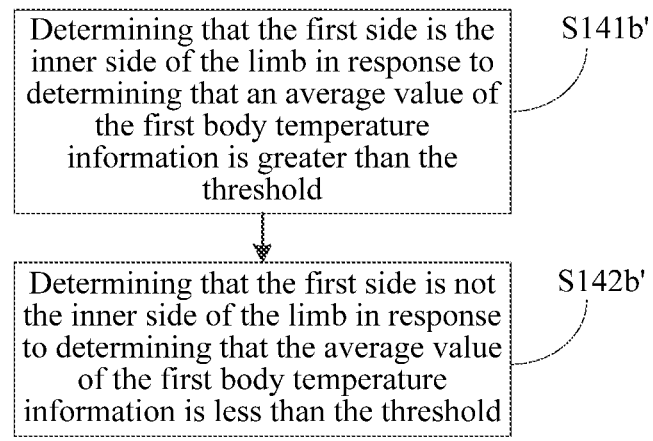
FIG. 8 is a flowchart of part of S140 of FIG. 1 according to an embodiment of the present application.

In some embodiments, the reference information may be a threshold determined according to body temperature information of the inner side and body temperature information of the outer side of the limb. Specifically, referring to FIG. 8, step S140*b* may comprise:

S141*b'*: determining that the first side is the inner side of the limb in response to determining that an average value of the first body temperature information is greater than the threshold; and S142*b'*: determining that the first side is not the inner side of the limb in response to determining that the average value of the first body temperature information is less than the threshold.

For example, body temperature information of the inner side of the limb and body temperature information of the outer side of the limb are pre-acquired and analyzed. Suppose that an average value of the body temperature information of the inner side falls within a first interval ($I_{min}$, $I_{max}$) and suppose that an average value of the body temperature information of the outer side falls within a second interval ($O_{min}$, $O_{max}$), $O_{max} < I_{min}$, it can be determined that the threshold is M, and $O_{max} < M < I_{min}$. That is to say, the threshold M is a value between the first interval and the second interval.

Therefore, if an average value of the first body temperature information is greater than the threshold M, it can be considered that the average value falls within the first interval, and the first side is the inner side of the limb; if the average value of the first body temperature information is less than the threshold M, it can be considered that the average value falls within the second interval, and the first side is not the inner side of the limb, that is, is the outer side of the limb.

It should be noted that, if the device for determining inner and outer sides of limbs contacts the inner side and the outer side of the limb at the same time and heat conduction passing through the device exists, acquisition time of the first body temperature information and the second body temperature information can be completed within a predetermined time that begins from wearing the device, that is, should be completed before the Time $t_1$ in FIG. 6, so as to avoid wrong identification caused by merging of the two body temperature curves.

c) The first somatosensory information may include PH information of the first side, which can be first PH information. Step S140 can comprise the following to process first PH information:

S140*c*: determining whether the first side is the inner side of the limb according to the first PH information and reference information.

Figure 9:
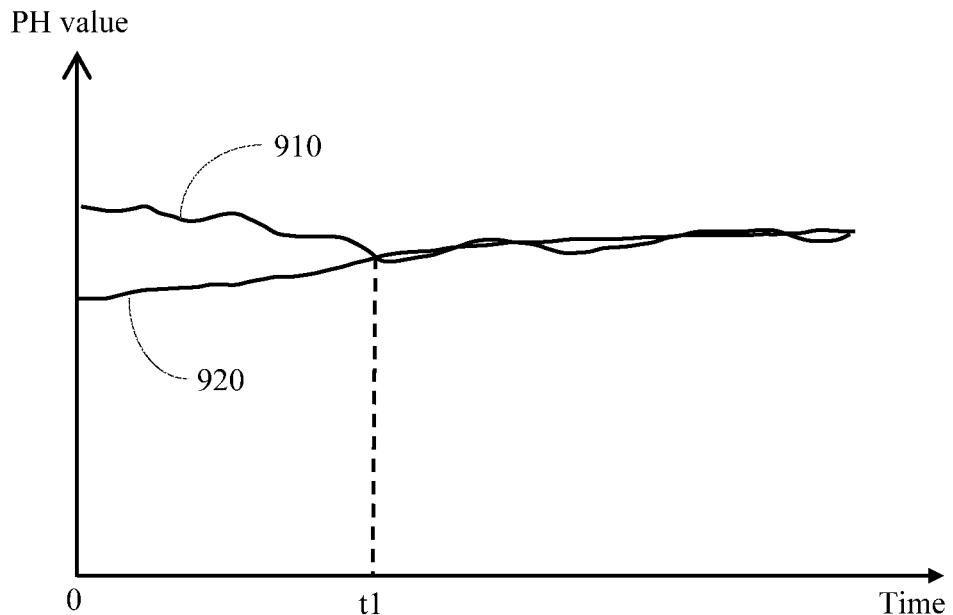
FIG. 9 is a schematic diagram of comparison of PH information on inner and outer sides of a wrist according to an embodiment of the present application.

The inventor has found in the study that, as the number of sweat glands of the inner side of the limb is more than that of the outer side of the limb, PH (i.e., PH value) of the inner side of the limb of the user is significantly less than that of the outer side of the limb. As shown in FIG. 9, the first curve 910 indicates a curve of PH information obtained by sampling PH signals of an outer side of a wrist of a user, and the second curve 920 indicates a curve of PH information obtained by sampling PH signals of an inner side of the wrist of the user. The horizontal axis indicates time, and the unit is second, while the longitudinal axis indicates PH.

It can be seen that the two curves in FIG. 9 have a significant difference before Time $t_2$, and after analysis, it can be obtained that the PH of the outer side of the wrist is significantly greater than that of the inner side of the wrist. After the Time $t_2$, the two curves gradually merge; this can be because the experiment simulates a real use environment of the user, and after the user wears the device for determining inner and outer sides of limbs for a period of time, the limb has sweat seepage thereon. In another experiment, influences of the sweat seepage are removed (e.g., the experiment is carried out in a cold environment), a PH curve finally obtained shows that the PH of the outer side of the wrist is always greater than that of the inner side of the wrist, and a difference thereof is about 0.3-0.4.

Similarly, the inventor has also found that the PH of the outer side of the palm is significantly greater than that of the inner side of the palm, and the PH of the outer side of the sole is significantly greater than that of the inner side of the sole. Therefore, a method of the present disclosure can achieve identification of inner and outer sides of limbs based on the principle.

In some embodiments, the reference information include second PH information acquired at a second side opposite to the first side on the limb. For example, two groups of somatosensory sensors can be set, corresponding PH information of the first side and the second side of the limb is acquired at the same time, and the PH information acquired at the second side is used as the reference information.

Figure 10:
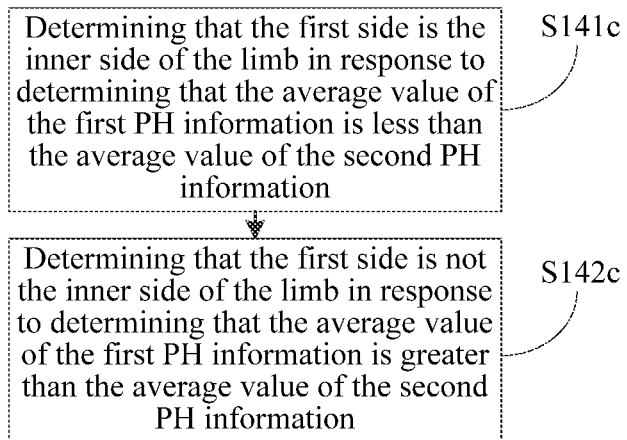
FIG. 10 is a flowchart of part of step S140 of FIG. 1 according to an embodiment of the present application.

In some embodiments, in step S140c, whether the first side is the inner side of the limb can be determined by comparing sizes of an average value of the first PH information and an average value of the second PH information. The average value of the first PH information can be an average value of PH values corresponding to a plurality of sampling points in the first PH information, and similarly, the average value of the second PH information can be an average value of PH values corresponding to a plurality of sampling points in the second PH information. By use of the average value, wrong identification caused by a sampling error occurring in a single sampling point can be avoided, thereby improving identification accuracy. Specifically, referring to FIG. 10, step S140c may comprise:

S141c: determining that the first side is the inner side of the limb in response to determining that the average value of the first PH information is less than the average value of the second PH information; and S142c: determining that the first side is not the inner side of the limb in response to determining that the average value of the first PH information is greater than the average value of the second PH information.

Figure 11:
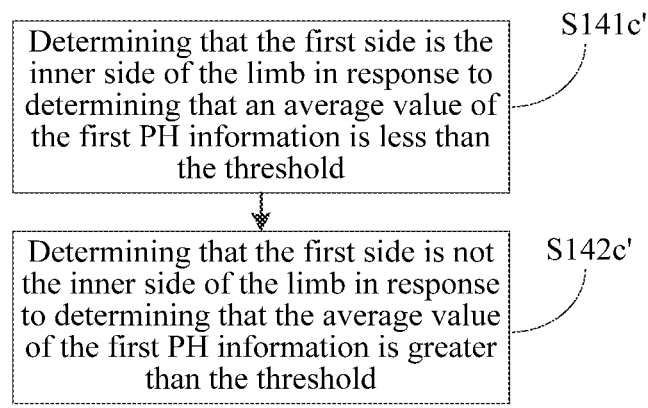
FIG. 11 is a flowchart of part of step S140 of FIG. 1 according to an embodiment of the present application.

In another implementation, the reference information may be a threshold determined according to PH information of the inner side and PH information of the outer side of the limb. Specifically, referring to FIG. 11, step S140c may comprise:

S141c': determining that the first side is the inner side of the limb in response to determining that an average value of the first PH information is less than the threshold; and S142c': determining that the first side is not the inner side of the limb in response to determining that the average value of the first PH information is greater than the threshold.

For example, PH information of the inner side of the limb and PH information of the outer side of the limb are pre-acquired and analyzed. Suppose that an average value of the PH information of the inner side falls within a first interval $(I_{min}, I_{max})$ and suppose that an average value of the PH information of the outer side falls within a second interval $(O_{min}, O_{max})$, $I_{max} < O_{min}$, it can be determined that the threshold is M, and $I_{max} < M < O_{min}$. That is to say, the threshold M is a value between the first interval and the second interval.

Therefore, if an average value of the first PH information is greater than the threshold M, it can be considered that the average value falls within the second interval, and the first side is the outer side of the limb; if the average value of the first PH information is less than the threshold M, it can be considered that the average value falls within the first interval, and the first side is not the outer side of the limb, that is, is the inner side of the limb.

It should be noted that, if the device for determining inner and outer sides of limbs contacts the inner side and the outer side of the limb at the same time and sweat seepage exists in the contacting portions, acquisition time of the first PH information and the second PH information should be completed within a predetermined time that begins from wearing the device, that is, should be completed before the Time $t_2$ in FIG. 9, i.e., completed before sweat seepage, so as to avoid wrong identification caused by merging of the two PH curves.

d) The first somatosensory information may include PPG information of the first side, that is, first PPG information. The first PPG information may be acquired in a reflection manner or a transmission manner. When the reflection manner is used, the first PPG information may be acquired by disposing a corresponding PPG sensor on the first side of the limb; when the transmission manner is used, a detection signal sent by a transmitting end of a corresponding PPG sensor, after passing through the first side of the limb, is received by a receiving end, but the detection signal does not pass through the second side opposite the first side. Step S140 can comprise the following to process PPG information:

S140d: determining whether the first side is the inner side of the limb according to the first PPG information and reference information.

Figure 12:
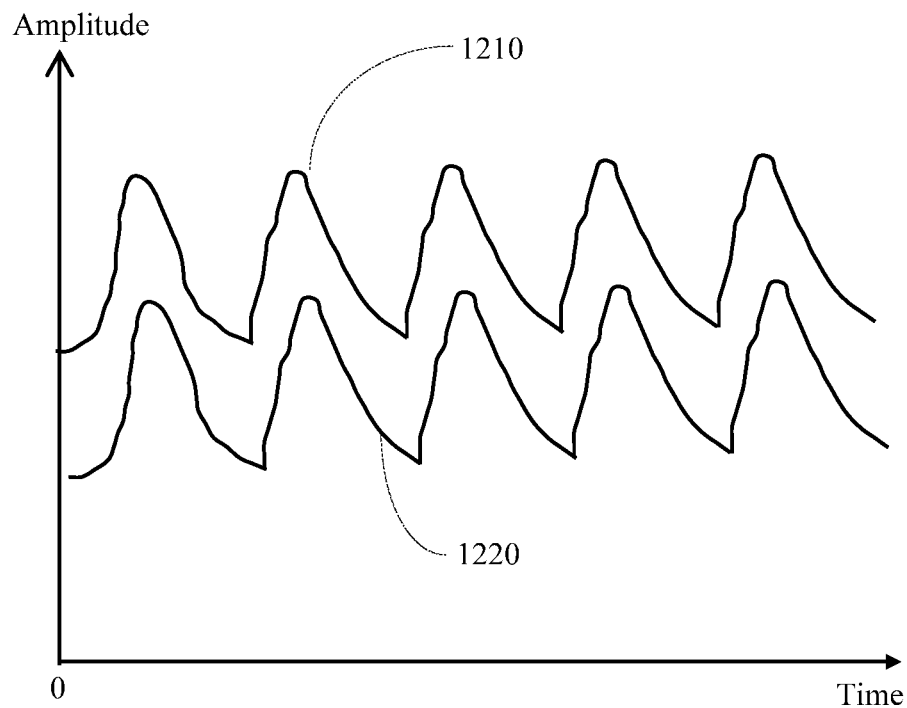
FIG. 12 is a schematic diagram of comparison of PPG information on inner and outer sides of a wrist in some embodiments of the present application.

The inventor has found in the study that, as the inner side of the limb has a higher light transmittance than the outer side of the limb, an average amplitude value of the PPG information of the inner side of the limb of the user will be higher than an average amplitude value of the PPG information of the outer side of the limb. As shown in FIG. 12, the first curve 1210 indicates a curve of PPG information obtained by sampling PPG signals of an inner side of a wrist of a user by using a first PPG sensor, and the second curve 1220 indicates a curve of PPG information obtained by sampling PPG signals of an outer side of the wrist of the user by using a second PPG sensor. The horizontal axis indicates time, and the unit is second, while the longitudinal axis indicates voltage amplitude value, and the unit is v. It can be seen that, the two curves in FIG. 12 have a significant difference, and after analysis, it can be obtained that the average amplitude value of the PPG information of the inner side of the wrist will be higher than the average amplitude value of the PPG information of the outer side of the wrist. The average amplitude value of the PPG information can be an average value of a plurality of PPG amplitude values.

Similarly, the inventor has also found that the average amplitude value of the PPG information of the inner side of the palm is significantly greater than the average amplitude value of the PPG information of the outer side of the palm, and the average amplitude value of the PPG information of the inner side of the sole is significantly greater than the average amplitude value of the PPG information of the outer side of the sole. Therefore, a method of the present disclosure can achieve identification of inner and outer sides of limbs based on the principle.

In some embodiments, the reference information include second PPG information acquired at a second side opposite the first side on the limb. For example, two groups of somatosensory sensors can be set, corresponding PPG information of the first side and the second side of the limb is acquired at the same time, and the PPG information acquired at the second side can be used as the reference information.

Figure 13:
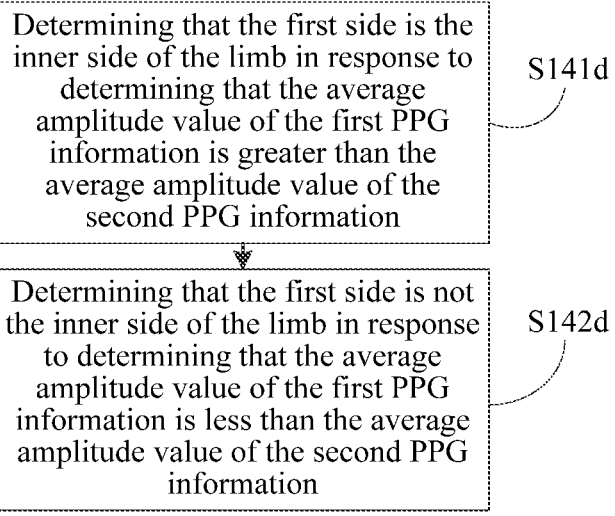
FIG. 13 is a flowchart of part of step S140 of FIG. 1 according to an embodiment of the present application.

In some embodiments, in step S140b, whether the first side is the inner side of the limb can be determined by comparing sizes of an average amplitude value of the first PPG information and an average amplitude value of the second PPG information. The average amplitude value of the first PPG information can be an average value of PPG amplitude values corresponding to a plurality of sampling points in the first PPG information, and similarly, the average amplitude value of the second PPG information can be an average value of PPG amplitude values corresponding to a plurality of sampling points in the second PPG information. By use of the average value, wrong identification caused by a sampling error occurring in a single sampling point can be avoided, thereby improving identification accuracy. Specifically, referring to FIG. 13, step S140d may comprise:

S141d: determining that the first side is the inner side of the limb in response to determining that the average amplitude value of the first PPG information is greater than the average amplitude value of the second PPG information; and S142d: determining that the first side is not the inner side of the limb in response to determining that the average amplitude value of the first PPG information is less than the average amplitude value of the second PPG information.

Figure 14:
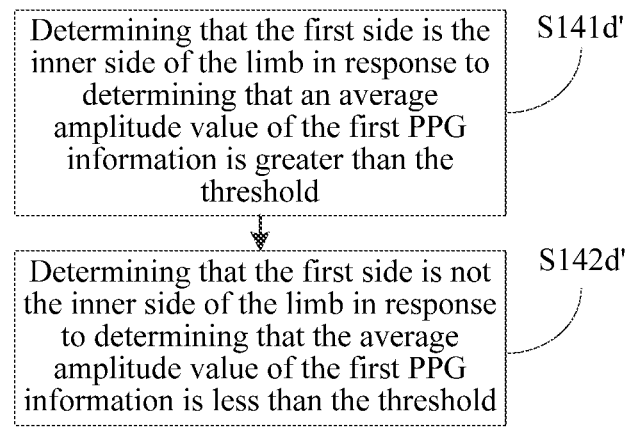
FIG. 14 is a flowchart of part of step S140 of FIG. 1 according to an embodiment of the present application.

In another implementation, the reference information may be a threshold determined according to PPG information of the inner side and PPG information of the outer side of the limb. Specifically, referring to FIG. 14, step S140d may comprise:

S141d': determining that the first side is the inner side of the limb in response to determining that an average amplitude value of the first PPG information is greater than the threshold; and S142d': determining that the first side is not the inner side of the limb in response to determining that the average amplitude value of the first PPG information is less than the threshold.

For example, PPG information of the inner side of the limb and PPG information of the outer side of the limb are pre-acquired and analyzed. Suppose that an average amplitude value of the PPG information of the inner side falls within a first interval $(I_{min}, I_{max})$ and suppose that an average amplitude value of the PPG information of the outer side falls within a second interval $(O_{min}, O_{max})$, $O_{max} < I_{min}$, it can be determined that the threshold is M, and $O_{max} < M < I_{min}$. That is to say, the threshold M is a value between the first interval and the second interval.

Therefore, if an average amplitude value of the first PPG information is greater than the threshold M, it can be considered that the average amplitude value falls within the first interval, and the first side is the inner side of the limb; if the average amplitude value of the first PPG information is less than the threshold M, it can be considered that the average amplitude value falls within the second interval, and the first side is not the inner side of the limb, that is, is the outer side of the limb.

e) The first somatosensory information may include humidity information of the first side, that is, first humidity information. Step S140 can comprise the following to process first humidity information:

S140e: determining whether the first side is the inner side of the limb according to the first humidity information and reference information.

The inventor has found in the study that, as the number of sweat glands of the inner side of the limb is more than that of the outer side of the limb, humidity of the inner side of the limb of the user will be higher than that of the outer side of the limb. As shown in FIG. 15, the first curve 1510 indicates a curve of humidity information obtained by sampling humidity signals of an inner side of a wrist of a user by using a first humidity sensor, and the second curve 1520 indicates a curve of humidity information obtained by sampling humidity signals of an outer side of the wrist of the user by using a second humidity sensor. The horizontal axis indicates time, and the unit is s, while the longitudinal axis indicates humidity. It can be seen that the two curves in FIG. 15 show that humidity of the inner side of the wrist is significantly greater than that of the outer side of the wrist.

Similarly, the inventor has also found that the humidity of the inner side of the palm is significantly greater than that of the outer side of the palm, and the humidity of the inner side of the sole is significantly greater than that of the outer side of the sole. Therefore, a method of the present disclosure can achieve identification of inner and outer sides of limbs based on the principle.

In some embodiments, the reference information include second humidity information acquired at a second side opposite the first side on the limb. For example, two groups of somatosensory sensors can be set, corresponding humidity information of the first side and the second side of the limb is acquired at the same time, and the humidity information acquired at the second side is used as the reference information.

In some embodiments, in step S140e, whether the first side is the inner side of the limb can be determined by comparing sizes of an average value of the first humidity information and an average value of the second humidity information. The average value of the first humidity information can be an average value of humidity values corresponding to a plurality of sampling points in the first humidity information, and similarly, the average value of the second humidity information can be an average value of humidity values corresponding to a plurality of sampling points in the second humidity information. By use of the average value, wrong identification caused by a sampling error occurring in a single sampling point can be avoided, thereby improving identification accuracy. Specifically, referring to FIG. 16, step S140e may comprise:

S141e: determining that the first side is the inner side of the limb in response to determining that the average value of the first humidity information is greater than the average value of the second humidity information; and S142e: determining that the first side is not the inner side of the limb in response to determining that the average value of the first humidity information is less than the average value of the second humidity information.

Figure 17:
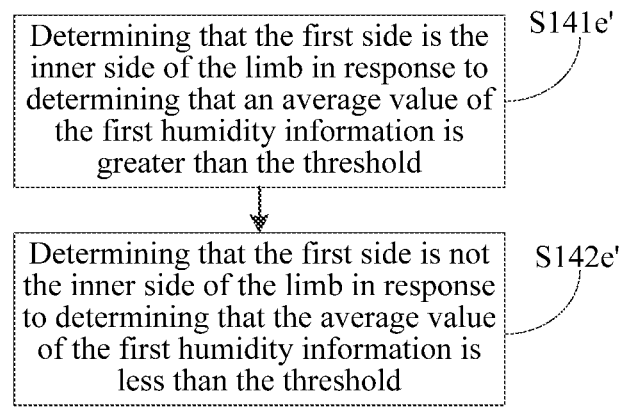
FIG. 17 is a flowchart of part of step S140 of FIG. 1 according to an embodiment of the present application.

In another implementation, the reference information may be a threshold determined according to humidity information of the inner side and humidity information of the outer side of the limb. Specifically, referring to FIG. 17, step S140e may comprise:

S141e': determining that the first side is the inner side of the limb in response to determining that an average value of the first humidity information is greater than the threshold; and S142e': determining that the first side is not the inner side of the limb in response to determining that the average value of the first humidity information is less than the threshold.

For example, humidity information of the inner side of the limb and humidity information of the outer side of the limb are pre-acquired and analyzed, suppose that an average value of the humidity information of the inner side falls within a first interval $(I_{min}, I_{max})$ and suppose that an average value of the humidity information of the outer side falls within a second interval $(O_{min}, O_{max})$, $O_{max} < I_{min}$, it can be determined that the threshold is M, and $O_{max} < M < I_{min}$. That is to say, the threshold M is a value between the first interval and the second interval.

Therefore, if an average value of the first humidity information is greater than the threshold M, it can be considered that the average value falls within the first interval, and the first side is the inner side of the limb; if the average value of the first humidity information is less than the threshold M, it can be considered that the average value falls within the second interval, and the first side is not the inner side of the limb, that is, is the outer side of the limb.

f) The first somatosensory information may include blood oxygen information of the first side, that is, first blood oxygen information. The blood oxygen information may be blood oxygen saturation, which can be acquired through a reflection manner or a transmission manner. For example, when the first blood oxygen information is acquired in the reflection manner, the first blood oxygen information can be acquired by disposing a corresponding blood oxygen sensor on the first side of the limb; when the first blood oxygen information is acquired in the transmission manner, a detection signal sent by a transmitting end of a corresponding blood oxygen sensor, after passing through the first side of the limb, is received by a receiving end, but the detection signal does not pass through the second side opposite the first side. Step S140 can further comprise the following to process first blood oxygen information:

S140f: determining whether the first side is the inner side of the limb according to the first blood oxygen information and reference information.

Figure 18:
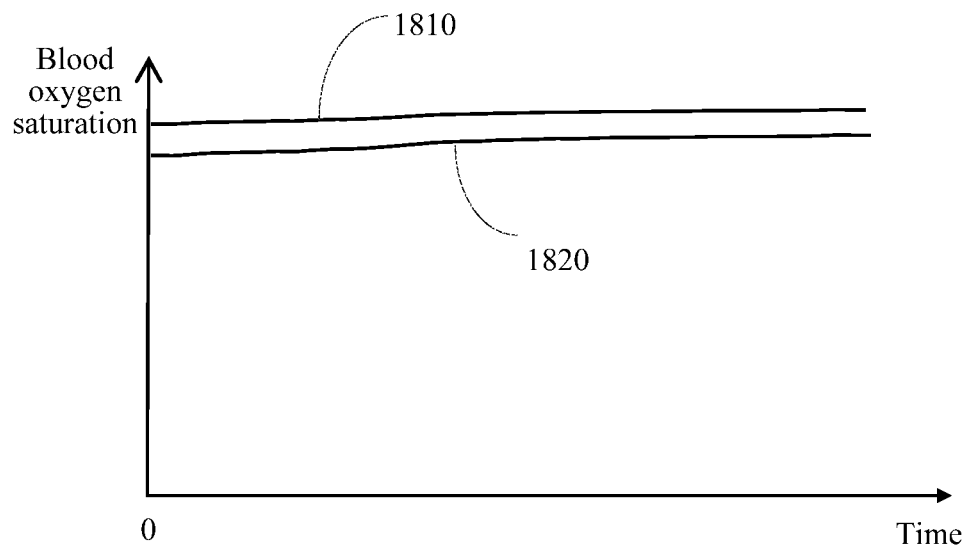
FIG. 18 is a schematic diagram of comparison of blood oxygen information on inner and outer sides of a wrist in some embodiments of the present application.

The inventor has found in the study that blood oxygen saturation is generally measured according to the amount of light with different wavelengths absorbed by blood in blood vessels. The number of vein vessels of the inner side of the limb is significantly more than that of the outer side of the limb, and arterial vessels are distributed deeper and are generally located at a middle part between the inner side and the outer side of the limb; therefore, an average value of blood oxygen information measured at the inner side of the limb of the user will be higher than an average value of blood oxygen information measured at the outer side of the limb. As shown in FIG. 18, the first curve 1810 indicates a curve of blood oxygen information obtained by sampling blood oxygen signals of an inner side of a wrist of a user by using a first blood oxygen sensor, and the second curve 1820 indicates a curve of blood oxygen information obtained by sampling blood oxygen signals of an outer side of the wrist of the user by using a second blood oxygen sensor. The horizontal axis indicates time, and the unit is second, while the longitudinal axis indicates blood oxygen saturation. It can be seen that the two curves in FIG. 18 have a significant difference, and after analysis, it can be obtained that the average value of the blood oxygen information of the inner side of the wrist will be higher than the average value of the blood oxygen information of the outer side of the wrist. The average value of the blood oxygen information can be an average value of blood oxygen saturation corresponding to a plurality of sampling points.

Similarly, the inventor has also found that the average value of the blood oxygen information of the inner side of the palm is significantly greater than the average value of the blood oxygen information of the outer side of the palm, and the average value of the blood oxygen information of the inner side of the sole is significantly greater than the average value of the blood oxygen information of the outer side of the sole. Therefore, a method of the present disclosure can achieve identification of inner and outer sides of limbs based on the principle.

In some embodiments, the reference information include second blood oxygen information acquired at a second side opposite the first side on the limb. For example, two groups of somatosensory sensors can be set, corresponding blood oxygen information of the first side and the second side of the limb is acquired at the same time, and the blood oxygen information acquired at the second side is used as the reference information.

Figure 19:
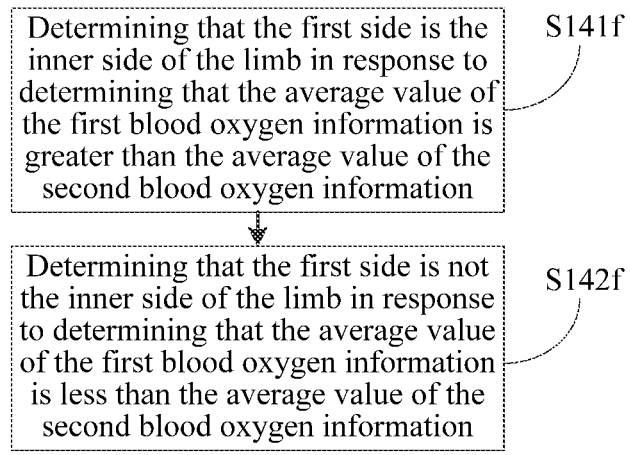
FIG. 19 is a flowchart of part of step S140 of FIG. 1 according to an embodiment of the present application.

In some embodiments, in step S140f, whether the first side is the inner side of the limb can be identified by comparing sizes of an average value of the first blood oxygen information and an average value of the second blood oxygen information. The average value of the first blood oxygen information can be an average value of blood oxygen saturation corresponding to a plurality of sampling points in the first blood oxygen information, and similarly, the average value of the second blood oxygen information can be an average value of blood oxygen saturation corresponding to a plurality of sampling points in the second blood oxygen information. By use of the average value, wrong identification caused by a sampling error occurring in a single sampling point can be avoided, thereby improving identification accuracy. Specifically, referring to FIG. 19, step S140f may comprise:

S141f: determining that the first side is the inner side of the limb in response to determining that the average value of the first blood oxygen information is greater than the average value of the second blood oxygen information; and S142f: determining that the first side is not the inner side of the limb in response to determining that the average value of the first blood oxygen information is less than the average value of the second blood oxygen information.

Figure 20:
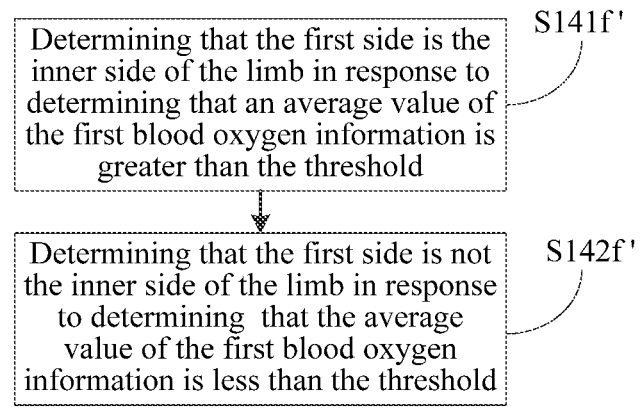
FIG. 20 is a flowchart of part of step S140 of FIG. 1 according to an embodiment of the present application.

In some embodiments, the reference information may be a threshold determined according to blood oxygen information of the inner side and blood oxygen information of the outer side of the limb. Specifically, referring to FIG. 20, step S140f may comprise:

S141f': determining that the first side is the inner side of the limb in response to determining that an average value of the first blood oxygen information is greater than the threshold; and S142f': determining that the first side is not the inner side of the limb in response to determining that the average value of the first blood oxygen information is less than the threshold.

For example, blood oxygen information of the inner side of the limb and blood oxygen information of the outer side of the limb can be pre-acquired and analyzed. Suppose that an average value of the blood oxygen information of the inner side falls within a first interval ($I_{min}$, $I_{max}$) and suppose that an average value of the blood oxygen information of the outer side falls within a second interval ($O_{min}$, $O_{max}$), $O_{max} < I_{min}$, it can be determined that the threshold is M, and $O_{max} < M < I_{min}$. That is to say, the threshold M is a value between the first interval and the second interval.

Therefore, if an average value of the first blood oxygen information is greater than the threshold M, it can be considered that the average value falls within the first interval, and the first side is the inner side of the limb; if the average value of the first blood oxygen information is less than the threshold M, it can be considered that the average value falls within the second interval, and the first side is not the inner side of the limb, that is, is the outer side of the limb.

g) The first somatosensory information may include fat information of the first side, that is, first fat information. The fat information may be a fat rate, for example, the first fat information may be a fat rate measured and acquired at the first side of the limb by a corresponding fat measurement sensor. Step S140 can comprise the following to process first fat information:

S140g: determining whether the first side is the inner side of the limb according to the first fat information and reference information.

Figures 21, 22A:
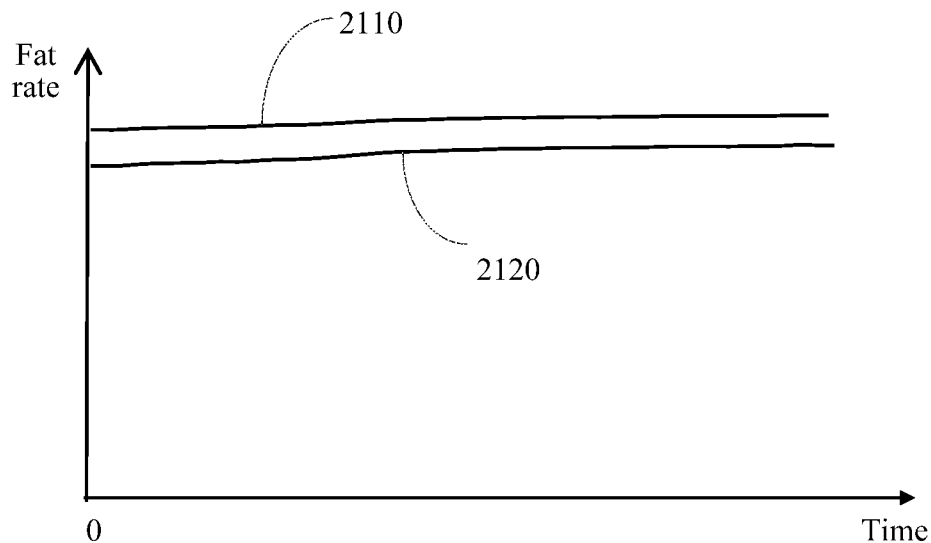
FIG. 21 is a schematic diagram of comparison of fat information on inner and outer sides of a wrist in some embodiments of the present application.
FIG. 22a is a flowchart of part of step S140 of FIG. 1 according to an embodiment of the present application.

The inventor has found in the study that, for the content of body fat, that is, the fat rate, the mainstream approach at present is to first measure body resistance and then speculate the content of fat according to the body resistance. The body water content is about 70%, most of the water exists in blood, lean meat and viscera, but water content in the fat is extremely low. Water in the body exhibits low resistance due to various dissolved components, but the fat exhibits high resistance, and thus the proportion of fat and water in the body affect the body resistance; if combined resistance of the fat and the water is taken into account, the more the fat is, the higher the body resistance is. A human limb, such as wrist, as a result of natural evolution, has higher fat content on an outer side than on an inner side. For the wrist, the high fat content on the outer side of the wrist can protect muscle and arterial vessels from being easily injured; at the same time, water content on the inner side of the wrist is significantly higher than that on the outer side of the wrist, and this is because the number of sweat glands on the inner side of the wrist is significantly higher than that on the outer side of the wrist. Therefore, by taking the two factors together, the fat rate of the outer side of the wrist is significantly higher than that of the inner side of the wrist. As shown in FIG. 21, the first curve 2110 indicates a curve of fat information obtained by sampling fat content of an inner side of a wrist of a user by using a first fat measurement sensor, and the second curve 2120 indicates a curve of fat information obtained by sampling fat content of an outer side of the wrist of the user by using a second fat measurement sensor. The horizontal axis indicates time, and the unit is s, while the longitudinal axis indicates fat rate. It can be seen that the two curves in FIG. 21 have a significant difference, and after analysis, it can be obtained that the average value of the fat information of the inner side of the wrist will be higher than the average value of the fat information of the outer side of the wrist. The average value of the fat information can be an average value of fat rates corresponding to a plurality of sampling points.

Similarly, the inventor has also found that the average value of the fat information of the outer side of the palm is significantly greater than that of the inner side of the palm, and the average value of the fat information of the outer side of the sole is significantly greater than that of the inner side of the sole. Therefore, a method of the present disclosure can achieve identification of inner and outer sides of limbs based on the principle.

In some embodiments, the reference information can be second fat information acquired at a second side opposite the first side on the limb. For example, two groups of somatosensory sensors can be set, corresponding fat information of the first side and the second side of the limb is acquired at the same time, and the fat information acquired at the second side is used as the reference information.

In some embodiments, in step S140g, whether the first side is the inner side of the limb is determined by comparing sizes of an average value of the first fat information and an average value of the second fat information. The average value of the first fat information can be an average value of fat rates corresponding to a plurality of sampling points in the first fat information, and similarly, the average value of the second fat information can be an average value of fat rates corresponding to a plurality of sampling points in the second fat information. By use of the average value, wrong identification caused by a sampling error occurring in a single sampling point can be avoided, thereby improving identification accuracy. Specifically, referring to FIG. 22a, step S140g may comprise:

S141g: determining that the first side is the inner side of the limb in response to determining that the average value of the first fat information is greater than the average value of the second fat information; and S142g: determining that the first side is not the inner side of the limb in response to determining that the average value of the first fat information is less than the average value of the second fat information.

Figure 22B:
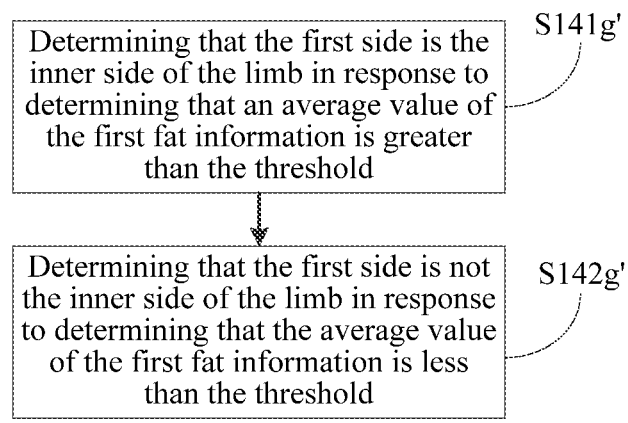
FIG. 22b is a flowchart of part of step S140 of FIG. 1 according to an embodiment of the present application.

In another implementation, the reference information may be a threshold determined according to fat information of the inner side and fat information of the outer side of the limb. Specifically, referring to FIG. 22b, step S140g may comprise:

S141g': determining that the first side is the inner side of the limb in response to determining that an average value of the first fat information is greater than the threshold; and S142g': determining that the first side is not the inner side of the limb in response to determining that the average value of the first fat information is less than the threshold.

For example, fat information of the inner side of the limb and fat information of the outer side of the limb are pre-acquired and analyzed. Suppose that an average value of the fat information of the inner side falls within a first interval ($I_{min}$, $I_{max}$) and suppose that an average value of the fat information of the outer side falls within a second interval ($O_{min}$, $O_{max}$), $I_{max} < O_{min}$, it can be determined that the threshold is M, and $I_{max} < M < O_{min}$. That is to say, the threshold M is a value between the first interval and the second interval.

Therefore, if an average value of the first fat information is less than the threshold M, it can be considered that the average value falls within the first interval, and the first side is the inner side of the limb; if the average value of the first fat information is greater than the threshold M, it can be considered that the average value falls within the second interval, and the first side is not the inner side of the limb, that is, is the outer side of the limb.

h) The first somatosensory information may include bioelectrical impedance information of the first side, that is, first bioelectrical impedance information. For example, the first bioelectrical impedance information may be bioelectrical impedance information measured and acquired at the first side of the limb by a corresponding bioelectrical impedance sensor. Step S140 can comprise the following to process first bioelectrical impedance information:

S140g: determining whether the first side is the inner side of the limb according to the first bioelectrical impedance information and reference information.

Figure 23A:
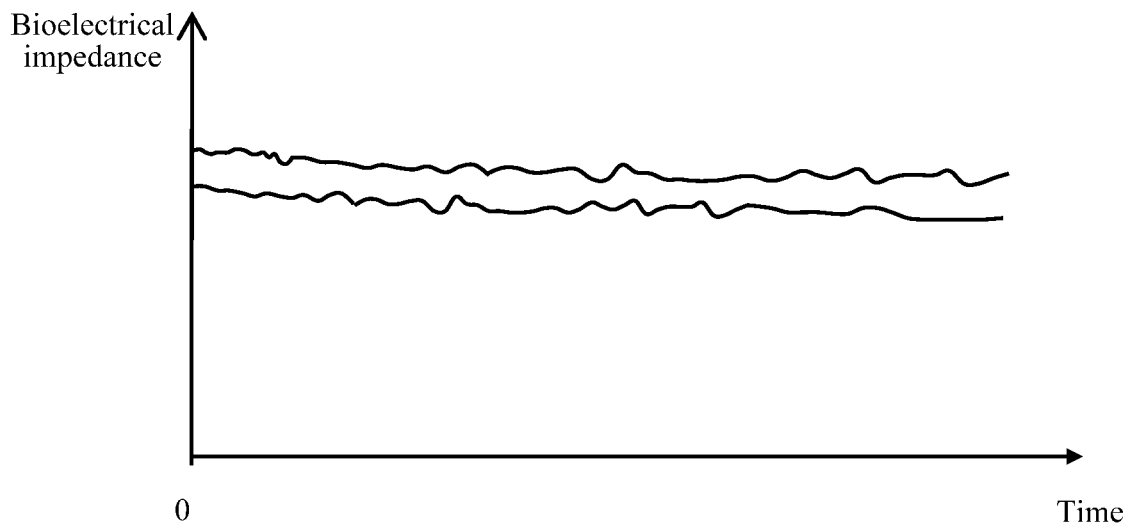
FIG. 23a is a schematic diagram of comparison of bioelectrical impedance information on inner and outer sides of a wrist according to an embodiment of the present application.

The inventor has found in the study that, as the outer side of the limb of the user is stronger and rougher than the inner side of the limb and surface layers of the skin are thicker, bioelectrical impedance of the outer side of the limb is higher than that of the inner side of the limb. Moreover, bioelectrical impedance of the inner side of the limb of the user and bioelectrical impedance of the outer side of the limb have a statistical significant difference, that is, their P value is less than or equal to 0.05. As shown in FIG. 23a, the upper curve indicates a curve of bioelectrical impedance information obtained by sampling bioelectrical impedance signals of an outer side of a wrist of a user, and the lower curve indicates a curve of bioelectrical impedance information obtained by sampling bioelectrical impedance signals of an inner side of the wrist of the user. The horizontal axis indicates time, and the unit is s, while the longitudinal axis indicates bioelectrical impedance amplitude value, and the unit is ohm. It can be seen that the two curves have a significant difference, and after analysis, it can be obtained that the average amplitude value of the bioelectrical impedance of outer side of the wrist is significantly greater than that of the inner side of the wrist. Similarly, the inventor has also found that the average amplitude value of the bioelectrical impedance of the outer side of the palm is significantly greater than that of the inner side of the palm, and the average amplitude value of the bioelectrical impedance of the outer side of the sole is significantly greater than that of the inner side of the sole. Therefore, a method of the present disclosure can achieve identification of inner and outer sides of limbs based on the principle.

In some embodiments, the method further comprises:

S140h: acquiring second bioelectrical impedance information at a second side opposite the first side on the limb as the reference information.

That is to say, the reference information include second bioelectrical impedance information acquired at a second side opposite the first side on the limb. For example, two groups of somatosensory sensors can be set, corresponding bioelectrical impedance information of the first side and the second side of the limb is acquired at the same time, and the bioelectrical impedance information acquired at the second side is used as the reference information.

Figure 23B:
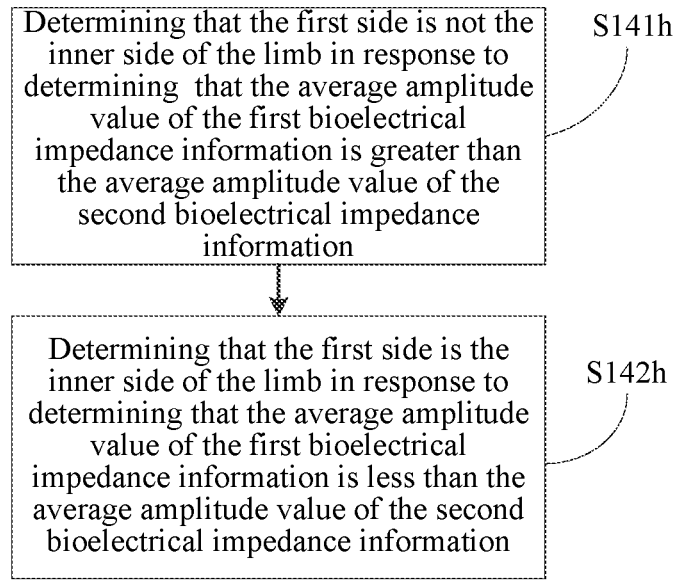
FIG. 23b is a schematic flowchart of step S140 of FIG. 1 according to an embodiment of the present application.

In some embodiments, in step S140h, whether the first side is the inner side of the limb can be determined by comparing sizes of an average amplitude value of the first bioelectrical impedance information and an average amplitude value of the second bioelectrical impedance information. Specifically, referring to FIG. 23b, step S140h may comprise:

S141h: determining that the first side is not the inner side of the limb in response to determining that the average amplitude value of the first bioelectrical impedance information is greater than the average amplitude value of the second bioelectrical impedance information; and S142h: determining that the first side is the inner side of the limb in response to determining that the average amplitude value of the first bioelectrical impedance information is less than the average amplitude value of the second bioelectrical impedance information.

Figure 23C:
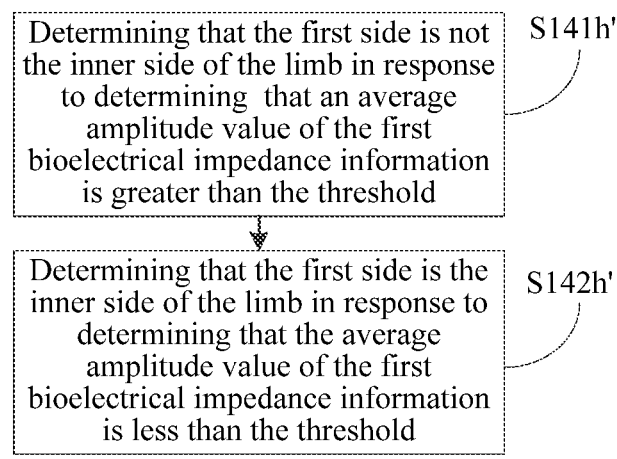
FIG. 23c is a schematic flowchart of step S140 of FIG. 1 according to an embodiment of the present application.

In another implementation, the reference information may be a threshold determined according to bioelectrical impedance information of the inner side and bioelectrical impedance information of the outer side of the limb. Specifically, referring to FIG. 23c, step S140h may comprise:

S141h': determining that the first side is not the inner side of the limb in response to determining that an average amplitude value of the first bioelectrical impedance information is greater than the threshold; and S142h': determining that the first side is the inner side of the limb in response to determining that the average amplitude value of the first bioelectrical impedance information is less than the threshold.

For example, bioelectrical impedance information of the inner side of the limb and bioelectrical impedance information of the outer side of the limb are pre-acquired and are analyzed, suppose that an average amplitude value of the bioelectrical impedance information of the inner side falls within a first interval ($I_{min}$, $I_{max}$) and suppose that an average amplitude value of the bioelectrical impedance information of the outer side falls within a second interval ($O_{min}$, $O_{max}$), $I_{max}<O_{min}$, it can be determined that the threshold is M, and $I_{max}<M<O_{min}$. That is to say, the threshold M is a value between the first interval and the second interval.

Therefore, if an average amplitude value of the first bioelectrical impedance information is greater than the threshold M, it can be considered that the average value falls within the second interval, and the first side is not the inner side of the limb, that is, is the outer side of the limb; if the average amplitude value of the first bioelectrical impedance information is less than the threshold M, it can be considered that the average value falls within the first interval, and the first side is the inner side of the limb.

Figure 24:
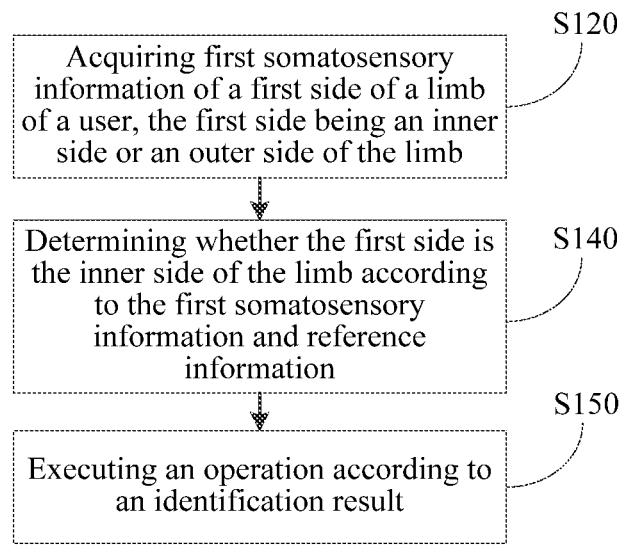
FIG. 24 is a flowchart of a method for determining inner and outer sides of limbs according to an embodiment of the present application.

Referring to FIG. 24, in some embodiments, the method may further comprise:

S150: executing an operation according to an identification result.

For example, if it is displayed according to an identification result that the first side is the inner side of the limb, somatosensory signals of the user can be continuously acquired at the first side; if it is displayed that the first side is not the inner side of the limb, acquisition of the somatosensory signals of the user can be stopped at the first side, while the somatosensory signals of the user are acquired at a second side opposite the first side. The somatosensory signals comprise body skin conductive information, body temperature information, PH information, PPG information, humidity information, blood oxygen information, fat information and the like.

Suppose that a smart watch that a user wears is provided with one group of somatosensory sensors respectively corresponding to the inner side and the outer side of the limb, the user does not need to consider the wearing manner when wearing the watch, and the smart watch will automatically stop contacting operation of the somatosensory sensors on the outer side of the limb but ensure contacting operation of the sensors on the inner side of the limb, thereby enhancing user experience.

In addition, one embodiment of the present application further provides a computer readable medium, comprising a computer readable instruction which performs the following operations when being executed: executing the operations of steps S120 and S140 of the method in an embodiment as shown in FIG. 1.

To sum up, the method according to the embodiment of the present application can identify, according to first somatosensory information of a first side of a limb of a user and reference information, whether the first side is an inner side of the limb, and can execute a corresponding operation according to an identification result, thereby enhancing user experience.

Figure 25:
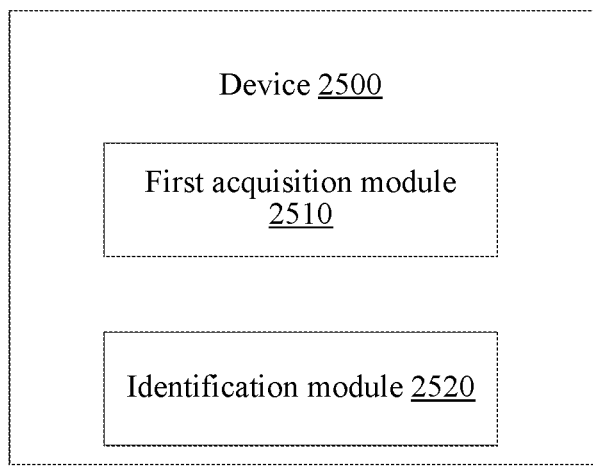
FIG. 25 is a modular structure diagram of a device for determining inner and outer sides of limbs according to an embodiment of the present application.

FIG. 25 is a modular structure diagram of the device for determining inner and outer sides of limbs according to one embodiment of the present application; the device for determining inner and outer sides of limbs may be disposed in a wearable device such as a smart wristband or a smart watch as a functional module, and certainly may also be used by a user as a separate wearable device. As shown in FIG. 25, the device 2500 may comprise:

a first acquisition module 2510, configured to acquire first somatosensory information of a first side of a limb of a user, the first side being an inner side or an outer side of the limb; and an identification module 2520, configured to identify whether the first side is the inner side of the limb according to the first somatosensory information and reference information.

According to a device of an embodiment of the present disclosure, first somatosensory information of a first side of a limb of a user is acquired, and then whether the first side is the inner side of the limb is determined according to the first somatosensory information and reference information, so as to provide a method for determining inner and outer sides of limbs, which facilitates a device that the user wears to perform automatic setting according to an identification result, thereby enhancing user experience.

Functions of the first acquisition module 2510 and the identification module 2520 are described below in detail in combination with specific implementations.

A first acquisition module 2510, configured to acquire first somatosensory information of a first side of a limb of a user, the first side being an inner side or an outer side of the limb.

The limb may comprise an upper limb and a lower limb of the user. Specifically, the inner side of the limb may be an inner side of a wrist, an inner side of a palm or an inner side of a sole, and correspondingly, the outer side of the limb may be an outer side of the wrist, an outer side of the palm or an outer side of the sole. As shown in FIG. 2, the inner side of the palm is a palm center 220 and a region corresponding to fingers on one side of the palm center 220 in FIG. 2, and the outer side of the palm is the back of the hand and a region corresponding to fingers on one side of the back of the hand; the inner side of the wrist is a first region 210 on the same side with the palm center 220 and located between the palm and a forearm in FIG. 2, the outer side of the wrist is opposite the first region 210, that is, a second region on the same side with the back of the hand and located between the palm and the forearm. The inner side of the sole is a region corresponding to the bottom of a foot, and the outer side of the sole is a region corresponding to the top of the foot.

The first side is the inner side or outer side of the wrist, or the inner side or outer side of the palm, or the inner side or outer side of the sole. For the sake of simplicity, description is given below mostly by taking that the first side is the inner side or outer side of the wrist as an example.

The first somatosensory information may be skin conductive information, body temperature information, PH information, PPG information, humidity information, blood oxygen information or fat information of the first side of the limb, which can be acquired through a corresponding somatosensory sensor in contact with the skin of the user, almost all current smart wristbands, smart watches and the like have the sensors, and thus implementation of the method will not increase hardware costs of the existing wearable devices.

An identification module 2520, configured to identify whether the first side is the inner side of the limb according to the first somatosensory information and reference information.

a) The first somatosensory information may be skin conductive information of the first side, i.e., first skin conductive information. The identification module 2520 can identify whether the first side is the inner side of the limb according to the first skin conductive information and reference information.

Figure 26:
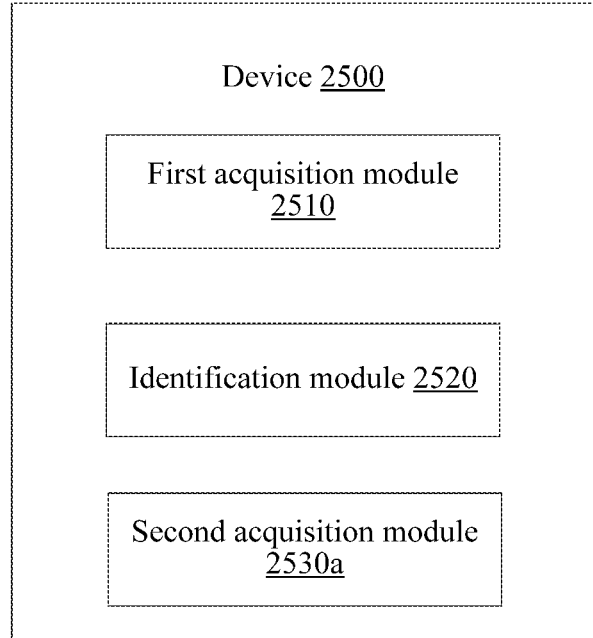
FIG. 26 is a modular structure diagram of a device for determining inner and outer sides of limbs according to an embodiment of the present application.

In some embodiments, the reference information include second skin conductive information acquired at a second side opposite the first side on the limb. Referring to FIG. 26, the device 2500 may further comprise:

a second acquisition module 2530a, configured to acquire second skin conductive information at a second side opposite the first side on the limb as the reference information.

In some embodiments, the identification module 2520 can identify whether the first side is the inner side of the limb by comparing sizes of an average value of the first skin conductive information and an average value of the second skin conductive information; specifically, the identification module 2520 can be configured to identify that the first side is the inner side of the limb in response to determining that the average value of the first skin conductive information is greater than the average value of the second skin conductive information; and identify that the first side is not the inner side of the limb in response to determining that the average value of the first skin conductive information is less than the average value of the second skin conductive information.

Figure 27:
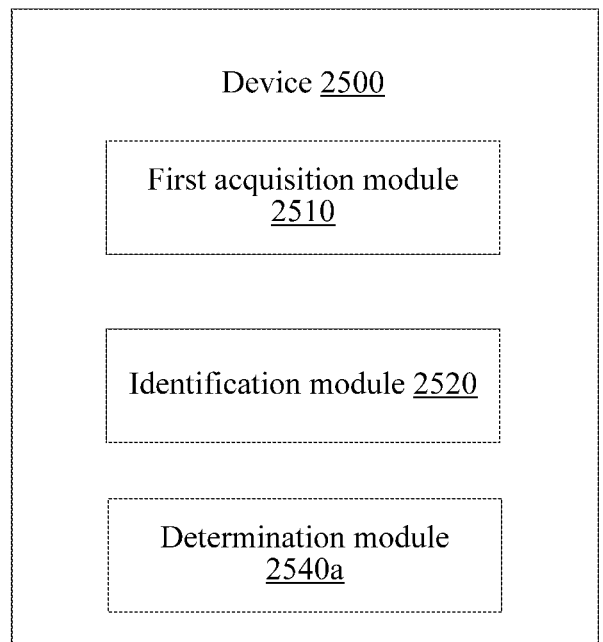
FIG. 27 is a modular structure diagram of a device for determining inner and outer sides of limbs according to an embodiment of the present application.

In another implementation, the reference information may be a threshold determined according to skin conductive information of the inner side and skin conductive information of the outer side of the limb. Specifically, as shown in FIG. 27, the device 2500 may comprise:

a determination module 2540a, configured to determine a threshold according to skin conductive information of the inner side and skin conductive information of the outer side of the limb as the reference information.

The identification module 2520 can be configured to identify that the first side is the inner side of the limb in response to determining that an average value of the first skin conductive information is greater than the threshold; and identify that the first side is not the inner side of the limb in response to determining that the average value of the first skin conductive information is less than the threshold.

For example, the determination module 2540a can pre-acquire and analyze skin conductive information of the inner side of the limb and skin conductive information of the outer side of the limb. Suppose that an average value of the skin conductive information of the inner side falls within a first interval $(I_{min}, I_{max})$ and suppose that an average value of the skin conductive information of the outer side falls within a second interval $(O_{min}, O_{max})$, $O_{max} < I_{min}$, it can be determined that the threshold is M, and $O_{max} < M < I_{min}$. That is to say, the threshold M is a value between the first interval and the second interval.

Therefore, if an average value of the first skin conductive information is greater than the threshold M, the identification module 2520 considers that the average value falls within the first interval, and the first side is the inner side of the limb; if the average value of the first skin conductive information is less than the threshold M, it can be considered that the average value falls within the second interval, and the first side is not the inner side of the limb, that is, is the outer side of the limb.

b) The first somatosensory information may be body temperature information of the first side, that is, first body temperature information. The identification module 2520 can identify whether the first side is the inner side of the limb according to the first body temperature information and reference information.

Figure 28:
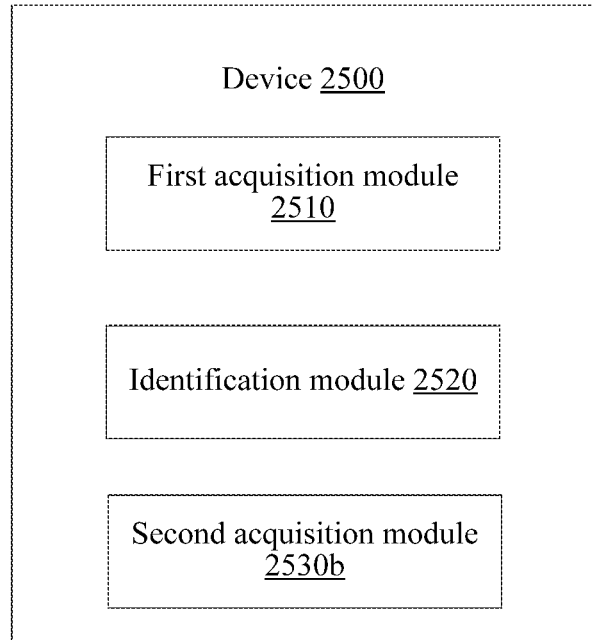
FIG. 28 is a modular structure diagram of a device for determining inner and outer sides of limbs according to an embodiment of the present application.

In some embodiments, the reference information include second body temperature information acquired at a second side opposite the first side on the limb. Referring to FIG. 28, the device 2500 may further comprise:

a second acquisition module 2530b, configured to acquire second body temperature information at a second side opposite the first side on the limb as the reference information.

In some embodiments, the identification module 2520 can identify whether the first side is the inner side of the limb by comparing sizes of an average value of the first body temperature information and an average value of the second body temperature information. The average value of the first body temperature information can be an average value of temperature values corresponding to a plurality of sampling points in the first body temperature information, and similarly, an average value of the second body temperature information can be an average value of temperature values corresponding to a plurality of sampling points in the second body temperature information. By use of the average value, wrong identification caused by a sampling error occurring in a single sampling point can be avoided, thereby improving identification accuracy. Specifically, the identification module 2520 can identify that the first side is the inner side of the limb in response to determining that the average value of the first body temperature information is greater than the average value of the second body temperature information; and identify that the first side is not the inner side of the limb in response to determining that the average value of the first body temperature information is less than the average value of the second body temperature information.

Figure 29:
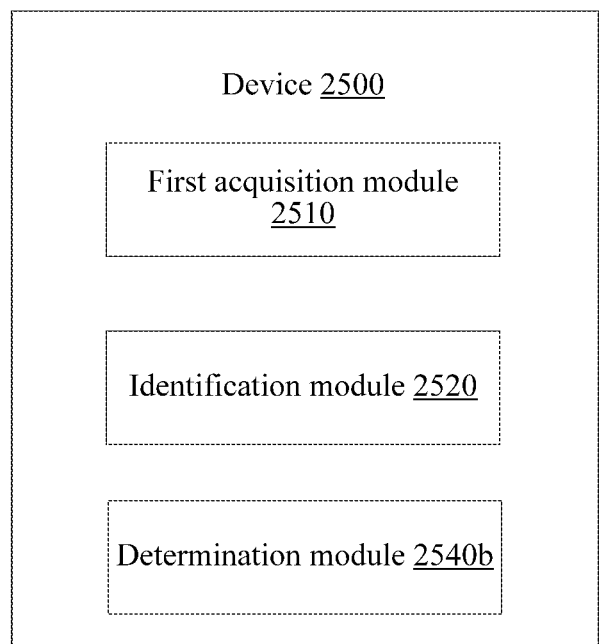
FIG. 29 is a modular structure diagram of a device for determining inner and outer sides of limbs according to an embodiment of the present application.

In another implementation, the reference information may be a threshold determined according to body temperature information of the inner side and body temperature information of the outer side of the limb. Specifically, referring to FIG. 29, the device 2500 may comprise:

a determination module 2540*b*, configured to determine a threshold according to body temperature information of the inner side and body temperature information of the outer side of the limb as the reference information.

The identification module 2520 can identify that the first side is the inner side of the limb in response to determining that an average value of the first body temperature information is greater than the threshold; and identify that the first side is not the inner side of the limb in response to determining that the average value of the first body temperature information is less than the threshold.

For example, the determination module 2540*b* can pre-acquire and analyze body temperature information of the inner side of the limb and body temperature information of the outer side of the limb. Suppose that an average value of the body temperature information of the inner side falls within a first interval ($I_{min}$, $I_{max}$) and suppose that an average value of the body temperature information of the outer side falls within a second interval ($O_{min}$, $O_{max}$), $O_{max} < I_{min}$, it can be determined that the threshold is M, and $O_{max} < M < I_{min}$. That is to say, the threshold M is a value between the first interval and the second interval.

Therefore, if an average value of the first body temperature information is greater than the threshold M, the identification module 2520 considers that the average value falls within the first interval, and the first side is the inner side of the limb; if the average value of the first body temperature information is less than the threshold M, it can be considered that the average value falls within the second interval, and the first side is not the inner side of the limb, that is, is the outer side of the limb.

It should be noted that, if the device 2500 for determining inner and outer sides of limbs contacts the inner side and the outer side of the limb at the same time and heat conduction passing through the device exists, acquisition time of the first body temperature information and the second body temperature information should be completed within a predetermined time that begins from wearing the device, that is, should be completed before the Time $t_1$ in FIG. 6, so as to avoid wrong identification caused by merging of the two body temperature curves.

c) The first somatosensory information may be PH information of the first side, that is, first PH information. The identification module 2520 can identify whether the first side is the inner side of the limb according to the first PH information and reference information.

Figure 30:
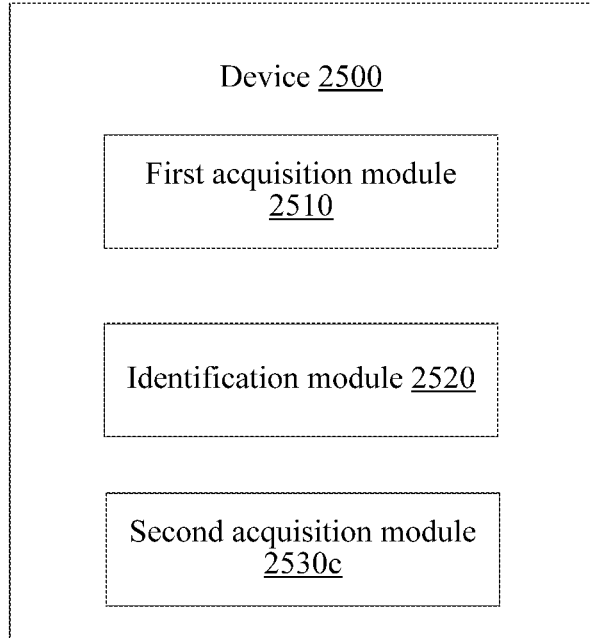
FIG. 30 is a modular structure diagram of a device for determining inner and outer sides of limbs according to an embodiment of the present application.

In some embodiments, the reference information include second PH information acquired at a second side opposite the first side on the limb. Referring to FIG. 30, the device 2500 may further comprise:

a second acquisition module 2530*c*, configured to acquire second PH information at a second side opposite the first side on the limb as the reference information.

In some embodiments, the identification module 2520 can identify whether the first side is the inner side of the limb by comparing sizes of an average value of the first PH information and an average value of the second PH information. The average value of the first PH information can be an average value of PH values corresponding to a plurality of sampling points in the first PH information, and similarly, the average value of the second PH information can be an average value of PH values corresponding to a plurality of sampling points in the second PH information. By use of the average value, wrong identification caused by a sampling error occurring in a single sampling point can be avoided, thereby improving identification accuracy. Specifically, the identification module 2520 can identify that the first side is the inner side of the limb in response to determining that the average value of the first PH information is less than the average value of the second PH information; and identify that the first side is not the inner side of the limb in response to determining that the average value of the first PH information is greater than the average value of the second PH information.

Figure 31:
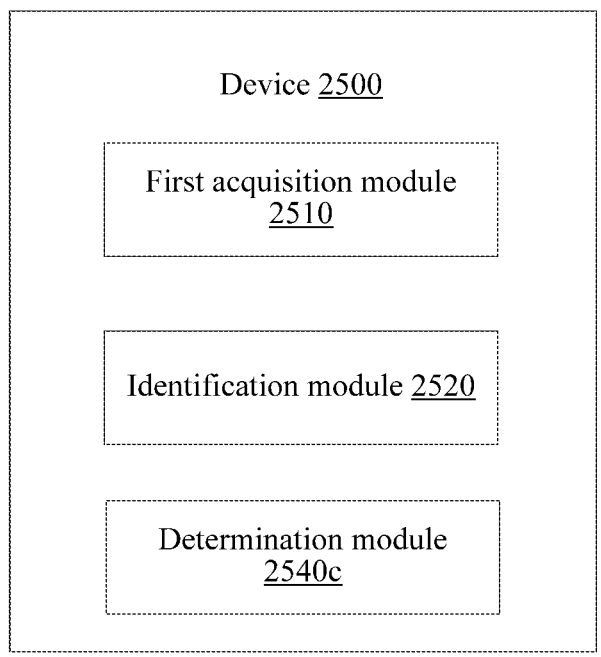
FIG. 31 is a modular structure diagram of a device for determining inner and outer sides of limbs according to an embodiment of the present application.

In another implementation, the reference information may be a threshold determined according to PH information of the inner side and PH information of the outer side of the limb. Specifically, referring to FIG. 31, the device 2500 may comprise:

a determination module 2540*c*, configured to determine a threshold according to PH information of the inner side and PH information of the outer side of the limb as the reference information.

The identification module 2520 can identify that the first side is the inner side of the limb in response to determining that an average value of the first PH information is less than the threshold; and identify that the first side is not the inner side of the limb in response to determining that the average value of the first PH information is greater than the threshold.

For example, the determination module 2540*c* can pre-acquire and analyze PH information of the inner side of the limb and PH information of the outer side of the limb, suppose that an average value of the PH information of the inner side falls within a first interval ($I_{min}$, $I_{max}$) and suppose that an average value of the PH information of the outer side falls within a second interval ($O_{min}$, $O_{max}$), $I_{max} < O_{min}$, it can be determined that the threshold is M, and $I_{max} < M < O_{min}$. That is to say, the threshold M is a value between the first interval and the second interval.

Therefore, if an average value of the first PH information is greater than the threshold M, the identification module 2520 considers that the average value falls within the second interval, and the first side is the outer side of the limb; if the average value of the first PH information is less than the threshold M, it can be considered that the average value falls within the first interval, and the first side is not the outer side of the limb, that is, is the inner side of the limb.

It should be noted that, if the device for determining inner and outer sides of limbs contacts the inner side and the outer side of the limb at the same time and sweat seepage exists in the contacting portions, acquisition time of the first PH information and the second PH information should be completed within a predetermined time that begins from wearing the device, that is, should be completed before the Time $t_2$ in FIG. 9, i.e., completed before sweat seepage, so as to avoid wrong identification caused by merging of the two PH curves.

d) The first somatosensory information may be PPG information of the first side, that is, first PPG information. The first PPG information may be acquired in a reflection manner or a transmission manner. When the reflection manner is used, the first PPG information may be acquired by disposing a corresponding PPG sensor on the first side of the limb; when the transmission manner is used, a detection signal sent by a transmitting end of a corresponding PPG sensor, after passing through the first side of the limb, is received by a receiving end, but the detection signal does not pass through the second side opposite the first side. The identification module 2520 can identify whether the first side is the inner side of the limb according to the first PPG information and reference information.

Figure 32:
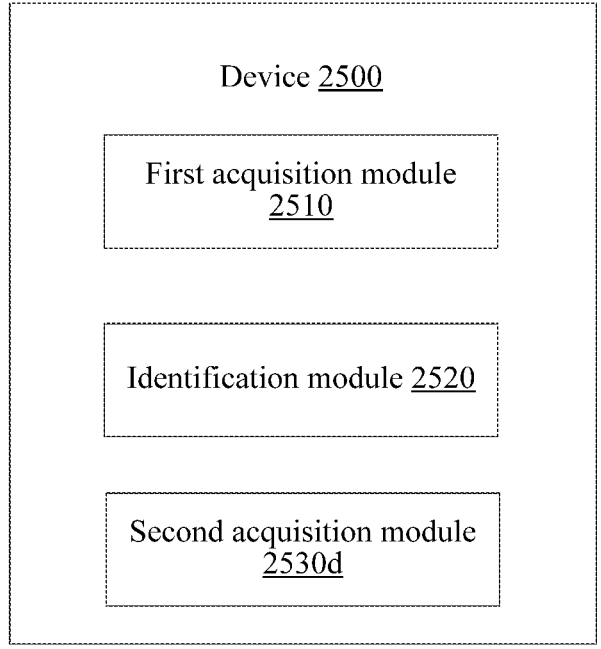
FIG. 32 is a modular structure diagram of a device for determining inner and outer sides of limbs according to an embodiment of the present application.

In some embodiments, the reference information include second PPG information acquired at a second side opposite the first side on the limb. Referring to FIG. 32, the device 2500 may further comprise:

a second acquisition module 2530d, configured to acquire second PPG information at a second side opposite the first side on the limb as the reference information.

In some embodiments, the identification module 2520 can identify whether the first side is the inner side of the limb by comparing sizes of an average amplitude value of the first PPG information and an average amplitude value of the second PPG information. The average amplitude value of the first PPG information can be an average value of PPG amplitude values corresponding to a plurality of sampling points in the first PPG information, and similarly, the average amplitude value of the second PPG information can be an average value of PPG amplitude values corresponding to a plurality of sampling points in the second PPG information. By use of the average value, wrong identification caused by a sampling error occurring in a single sampling point can be avoided, thereby improving identification accuracy. Specifically, the identification module 2520 can identify that the first side is the inner side of the limb in response to determining that the average amplitude value of the first PPG information is greater than the average amplitude value of the second PPG information; and identify that the first side is not the inner side of the limb in response to determining that the average amplitude value of the first PPG information is less than the average amplitude value of the second PPG information.

Figure 33:
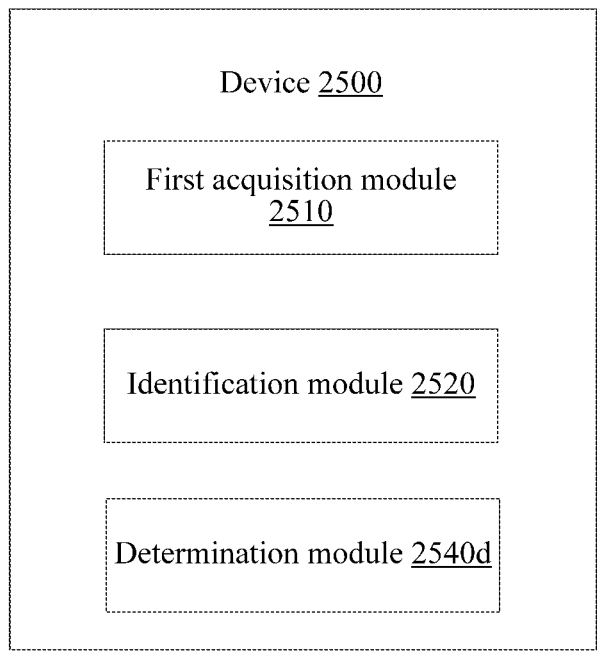
FIG. 33 is a modular structure diagram of a device for determining inner and outer sides of limbs according to an embodiment of the present application.

In another implementation, the reference information may be a threshold determined according to PPG information of the inner side and PPG information of the outer side of the limb. Specifically, referring to FIG. 33, the device 2500 may comprise:

a determination module 2540d, configured to determine a threshold according to PPG information of the inner side and PPG information of the outer side of the limb as the reference information The identification module 2520 can identify that the first side is the inner side of the limb in response to determining that an average amplitude value of the first PPG information is greater than the threshold; and identify that the first side is not the inner side of the limb in response to determining that the average amplitude value of the first PPG information is less than the threshold.

For example, the determination module 2540d can pre-acquire and analyze PPG information of the inner side of the limb and PPG information of the outer side of the limb, suppose that an average amplitude value of the PPG information of the inner side falls within a first interval ($I_{min}$, $I_{max}$) and suppose that an average amplitude value of the PPG information of the outer side falls within a second interval ($O_{min}$, $O_{max}$), $O_{max}<I_{min}$, it can be determined that the threshold is M, and $O_{max}<M<I_{min}$. That is to say, the threshold M is a value between the first interval and the second interval.

Therefore, if an average amplitude value of the first PPG information is greater than the threshold M, the identification module 2520 considers that the average amplitude value falls within the first interval, and the first side is the inner side of the limb; if the average amplitude value of the first PPG information is less than the threshold M, it can be considered that the average amplitude value falls within the second interval, and the first side is not the inner side of the limb, that is, is the outer side of the limb.

e) The first somatosensory information may be humidity information of the first side, that is, first humidity information. The identification module 2520 can identify whether the first side is the inner side of the limb according to the first humidity information and reference information.

Figure 34:
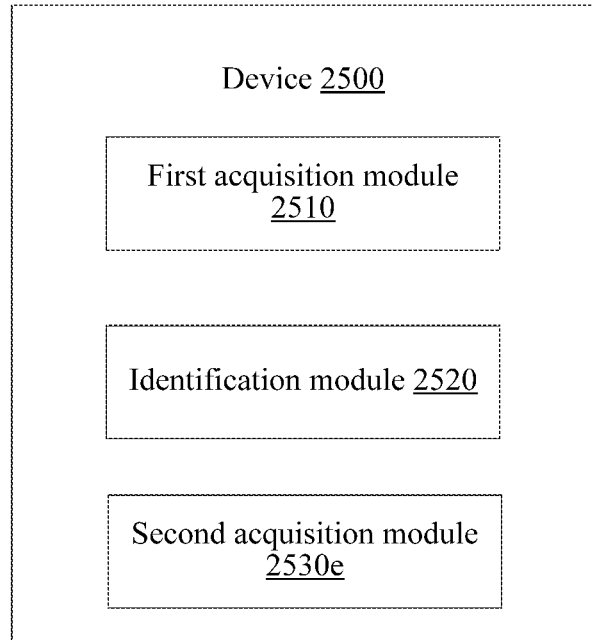
FIG. 34 is a modular structure diagram of a device for determining inner and outer sides of limbs according to an embodiment of the present application.

In some embodiments, the reference information include second humidity information acquired at a second side opposite the first side on the limb. Referring to FIG. 34, the device 2500 may further comprise:

a second acquisition module 2530e, configured to acquire second humidity information at a second side opposite the first side on the limb as the reference information.

In some embodiments, the identification module 2520 can identify whether the first side is the inner side of the limb by comparing sizes of an average value of the first humidity information and an average value of the second humidity information. The average value of the first humidity information can be an average value of humidity values corresponding to a plurality of sampling points in the first humidity information, and similarly, the average value of the second humidity information can be an average value of humidity values corresponding to a plurality of sampling points in the second humidity information. By use of the average value, wrong identification caused by a sampling error occurring in a single sampling point can be avoided, thereby improving identification accuracy. Specifically, the identification module 2520 can identify that the first side is the inner side of the limb in response to determining that the average value of the first humidity information is greater than the average value of the second humidity information; and identify that the first side is not the inner side of the limb in response to determining that the average value of the first humidity information is less than the average value of the second humidity information.

Figure 35:
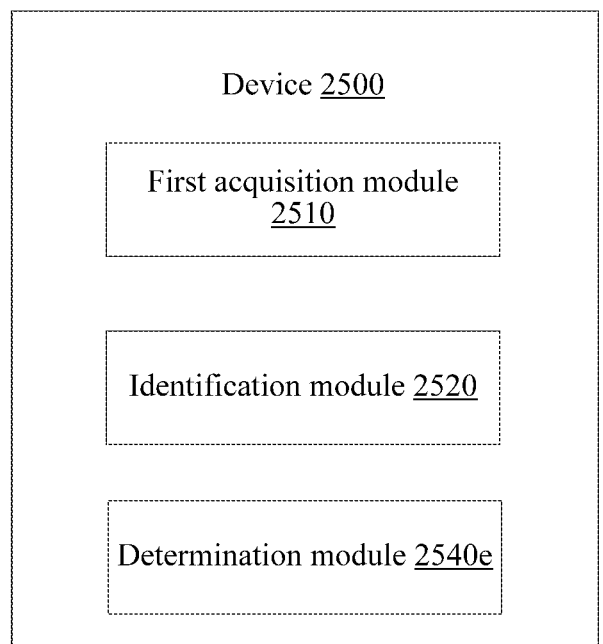
FIG. 35 is a modular structure diagram of a device for determining inner and outer sides of limbs according to an embodiment of the present application.

In another implementation, the reference information may be a threshold determined according to humidity information of the inner side and humidity information of the outer side of the limb. Specifically, referring to FIG. 35, the device 2500 may comprise:

a determination module 2540e, configured to determine a threshold according to humidity information of the inner side and humidity information of the outer side of the limb as the reference information.

The identification module 2520 can identify that the first side is the inner side of the limb in response to determining that an average value of the first humidity information is greater than the threshold; and identify that the first side is not the inner side of the limb in response to determining that the average value of the first humidity information is less than the threshold.

For example, the determination module 2540e can pre-acquire and analyze humidity information of the inner side of the limb and humidity information of the outer side of the limb, suppose that an average value of the humidity information of the inner side falls within a first interval ($I_{min}$, $I_{max}$) and suppose that an average value of the humidity information of the outer side falls within a second interval ($O_{min}$, $O_{max}$), $O_{max}<I_{min}$, it can be determined that the threshold is M, and $O_{max}<M<I_{min}$. That is to say, the threshold M is a value between the first interval and the second interval.

Therefore, if an average value of the first humidity information is greater than the threshold M, the identification module 2520 considers that the average value falls within the first interval, and the first side is the inner side of the limb; if the average value of the first humidity information is less than the threshold M, it can be considered that the average value falls within the second interval, and the first side is not the inner side of the limb, that is, is the outer side of the limb.

f) The first somatosensory information may be blood oxygen information of the first side, that is, first blood oxygen information. The blood oxygen information may be blood oxygen saturation, which can be acquired through a reflection manner or a transmission manner. For example, when the first blood oxygen information is acquired in the reflection manner, the first blood oxygen information can be acquired by disposing a corresponding blood oxygen sensor on the first side of the limb; when the first blood oxygen information is acquired in the transmission manner, a detection signal sent by a transmitting end of a corresponding blood oxygen sensor, after passing through the first side of the limb, is received by a receiving end, but the detection signal does not pass through the second side opposite the first side. The identification module 2520 can identify whether the first side is the inner side of the limb according to the first blood oxygen information and reference information.

Figure 36:
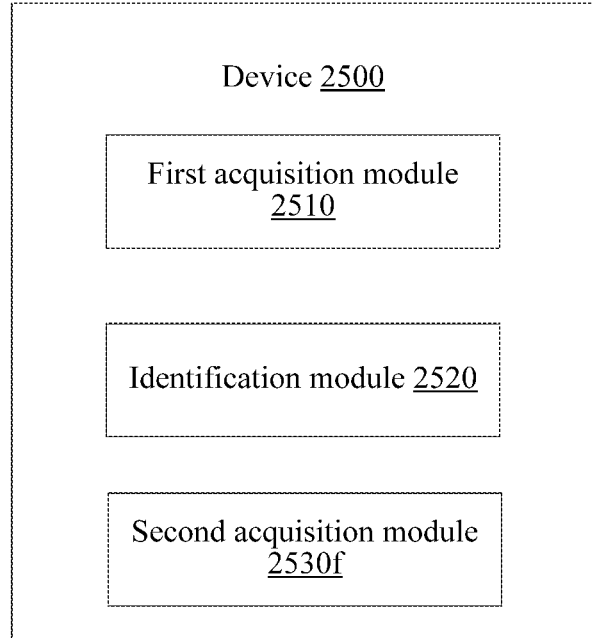
FIG. 36 is a modular structure diagram of a device for determining inner and outer sides of limbs according to an embodiment of the present application.

In some embodiments, the reference information include second blood oxygen information acquired at a second side opposite the first side on the limb. Referring to FIG. 36, the device 2500 may further comprise:

a second acquisition module 2530f, configured to acquire second blood oxygen information at a second side opposite the first side on the limb as the reference information.

In some embodiments, the identification module 2520 can identify whether the first side is the inner side of the limb is determined by comparing sizes of an average value of the first blood oxygen information and an average value of the second blood oxygen information. The average value of the first blood oxygen information can be an average value of blood oxygen saturation corresponding to a plurality of sampling points in the first blood oxygen information, and similarly, the average value of the second blood oxygen information can be an average value of blood oxygen saturation corresponding to a plurality of sampling points in the second blood oxygen information. By use of the average value, wrong identification caused by a sampling error occurring in a single sampling point can be avoided, thereby improving identification accuracy. Specifically, the identification module 2520 can identify that the first side is the inner side of the limb in response to determining that the average value of the first blood oxygen information is greater than the average value of the second blood oxygen information; and identify that the first side is not the inner side of the limb in response to determining that the average value of the first blood oxygen information is less than the average value of the second blood oxygen information.

Figure 37:
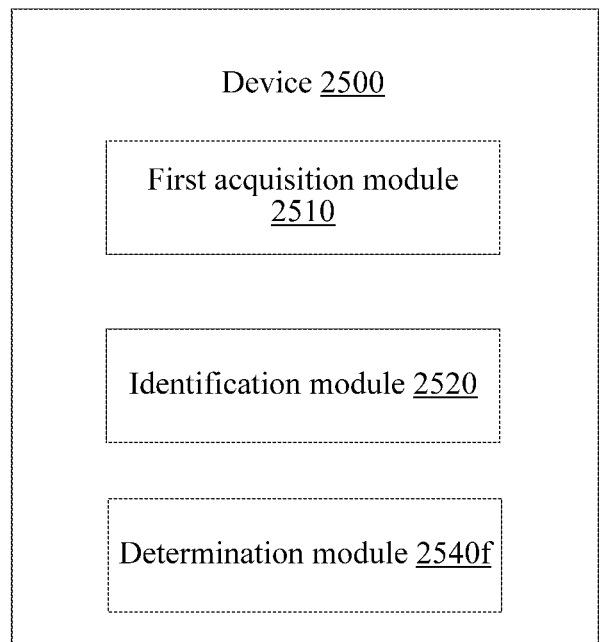
FIG. 37 is a modular structure diagram of a device for determining inner and outer sides of limbs according to an embodiment of the present application.

In another implementation, the reference information may be a threshold determined according to blood oxygen information of the inner side and blood oxygen information of the outer side of the limb. Specifically, referring to FIG. 37, the device 2500 may further comprise:

a determination module 2540f, configured to determine a threshold according to blood oxygen information of the inner side and blood oxygen information of the outer side of the limb as the reference information.

The identification module 2520 can identify that the first side is the inner side of the limb in response to determining that an average value of the first blood oxygen information is greater than the threshold; and identify that the first side is not the inner side of the limb in response to determining that the average value of the first blood oxygen information is less than the threshold.

For example, the determination module 2540f can pre-acquire and analyze blood oxygen information of the inner side of the limb and blood oxygen information of the outer side of the limb, suppose that an average value of the blood oxygen information of the inner side falls within a first interval ($I_{min}$, $I_{max}$) and suppose that an average value of the blood oxygen information of the outer side falls within a second interval ($O_{min}$, $O_{max}$), $O_{max}<I_{min}$, it can be determined that the threshold is M, and $O_{max}<M<I_{min}$. That is to say, the threshold M is a value between the first interval and the second interval.

Therefore, if an average value of the first blood oxygen information is greater than the threshold M, the identification module 2520 considers that the average value falls within the first interval, and the first side is the inner side of the limb; if the average value of the first blood oxygen information is less than the threshold M, it can be considered that the average value falls within the second interval, and the first side is not the inner side of the limb, that is, is the outer side of the limb.

g) The first somatosensory information may be fat information of the first side, that is, first fat information. The fat information may be a fat rate, for example, the first fat information may be a fat rate measured and acquired at the first side of the limb by a corresponding fat measurement sensor. The identification module 2520 can identify whether the first side is the inner side of the limb according to the first fat information and reference information.

Figure 38A:
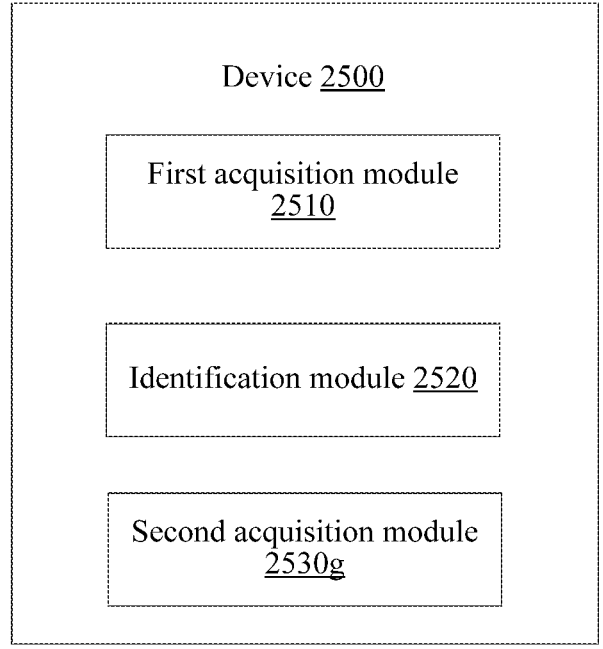
FIG. 38a is a modular structure diagram of a device for determining inner and outer sides of limbs according to an embodiment of the present application.

In some embodiments, the reference information include second fat information acquired at a second side opposite the first side on the limb. Referring to FIG. 38a, the device 2500 may further comprise:

a second acquisition module 2530g, configured to acquire second fat information at a second side opposite the first side on the limb as the reference information.

In some embodiments, the identification module 2520 can identify whether the first side is the inner side of the limb by comparing sizes of an average value of the first fat information and an average value of the second fat information. The average value of the first fat information can be an average value of fat rates corresponding to a plurality of sampling points in the first fat information, and similarly, the average value of the second fat information can be an average value of fat rates corresponding to a plurality of sampling points in the second fat information. By use of the average value, wrong identification caused by a sampling error occurring in a single sampling point can be avoided, thereby improving identification accuracy. Specifically, the identification module can identify that the first side is the inner side of the limb in response to determining that the average value of the first fat information is less than the average value of the second fat information; and identify that the first side is not the inner side of the limb in response to determining that the average value of the first fat information is greater than the average value of the second fat information.

Figure 38B:
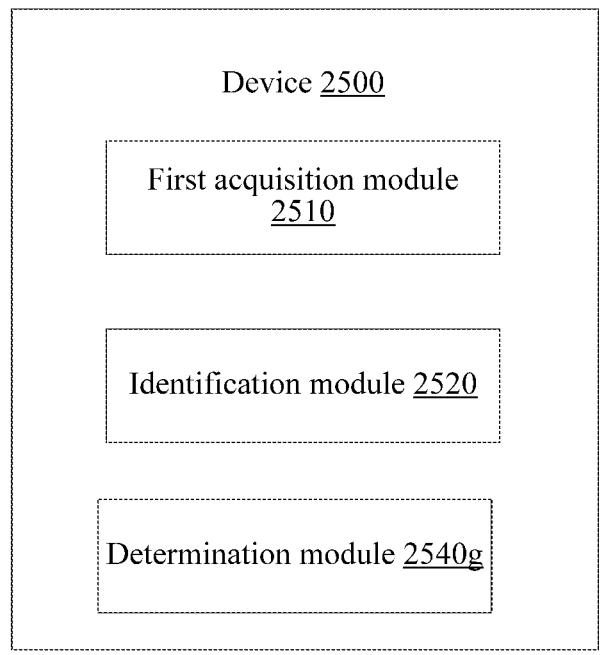
FIG. 38b is a modular structure diagram of a device for determining inner and outer sides of limbs according to an embodiment of the present application.

In another implementation, the reference information may be a threshold determined according to fat information of the inner side and fat information of the outer side of the limb. Specifically, referring to FIG. 38b, the device 2500 may comprise:

a determination module 2540g, configured to determine a threshold according to fat information of the inner side and fat information of the outer side of the limb as the reference information.

The identification module 2520 can identify that the first side is the inner side of the limb in response to determining that an average value of the first fat information is less than the threshold; and identify that the first side is not the inner side of the limb in response to determining that the average value of the first fat information is greater than the threshold.

For example, the determination module 2540g can pre-acquire and analyze fat information of the inner side of the limb and fat information of the outer side of the limb, suppose that an average value of the fat information of the inner side falls within a first interval ($I_{min}$, $I_{max}$) and suppose that an average value of the fat information of the outer side falls within a second interval ($O_{min}$, $O_{max}$), $I_{max} < O_{min}$, it can be determined that the threshold is M, and $I_{max} < M < O_{min}$. That is to say, the threshold M is a value between the first interval and the second interval.

Therefore, if an average value of the first fat information is less than the threshold M, the identification module 2520 considers that the average value falls within the first interval, and the first side is the inner side of the limb; if the average value of the first fat information is greater than the threshold M, it can be considered that the average value falls within the second interval, and the first side is not the inner side of the limb, that is, is the outer side of the limb.

h) The first somatosensory information may be bioelectrical impedance information of the first side, that is, first bioelectrical impedance information. The identification module 2520 is configured to identify whether the first side is the inner side of the limb according to the first bioelectrical impedance information and reference information.

Figure 39A:
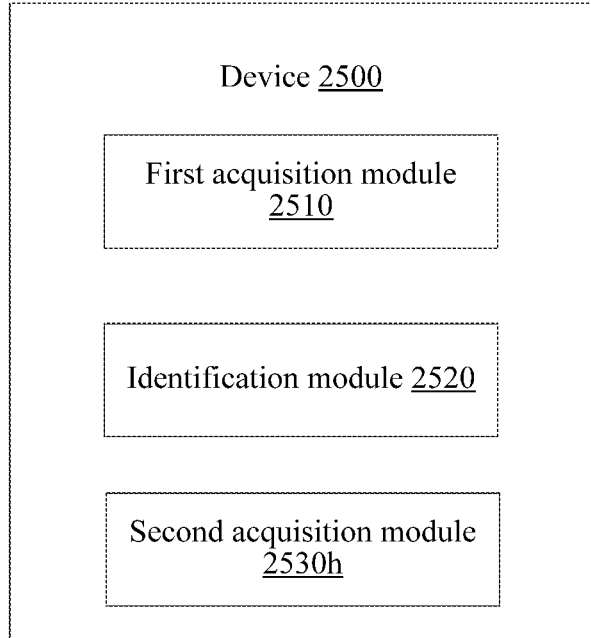
FIG. 39a is a modular structure diagram of a device for determining inner and outer sides of limbs according to an embodiment of the present application.

In some embodiments, the reference information include second bioelectrical impedance information acquired at a second side opposite the first side on the limb. Referring to FIG. 39a, the device 2500 may further comprise:

a second acquisition module 2530h, configured to acquire second bioelectrical impedance information at a second side opposite the first side on the limb as the reference information.

In some embodiments, the identification module 2520 can determine whether the first side is the inner side of the limb by comparing sizes of an average amplitude value of the first bioelectrical impedance information and an average amplitude value of the second bioelectrical impedance information. Specifically, the identification module 2520 can be configured to determine that the first side is not the inner side of the limb in response to determining that the average amplitude value of the first bioelectrical impedance information is greater than the average amplitude value of the second bioelectrical impedance information; and determine that the first side is the inner side of the limb in response to determining that the average amplitude value of the first bioelectrical impedance information is less than the average amplitude value of the second bioelectrical impedance information.

Figure 39B:
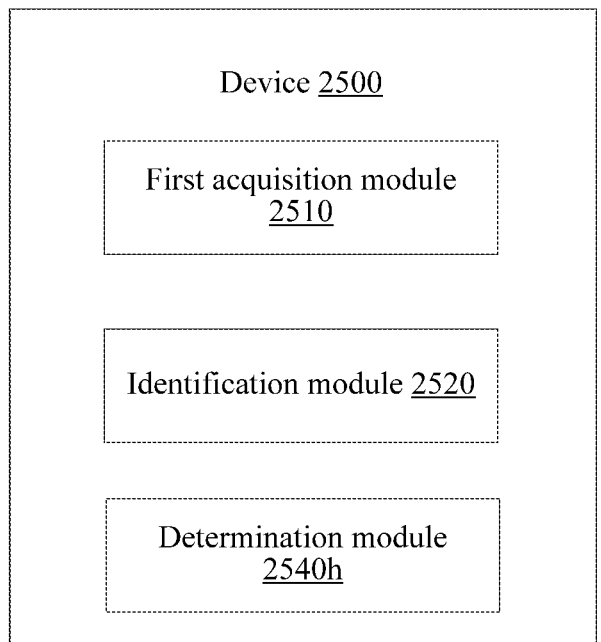
FIG. 39b is a modular structure diagram of a device for determining inner and outer sides of limbs according to an embodiment of the present application.

In another implementation, the reference information may be a threshold determined according to bioelectrical impedance information of the inner side and bioelectrical impedance information of the outer side of the limb. Specifically, referring to FIG. 39b, the device 2500 may comprise:

a determination module 2540h, configured to determine a threshold according to bioelectrical impedance information of the inner side and bioelectrical impedance information of the outer side of the limb as the reference information.

The identification module 2520 can be configured to determine that the first side is not the inner side of the limb in response to determining that an average amplitude value of the first bioelectrical impedance information is greater than the threshold; and determine that the first side is the inner side of the limb in response to determining that the average amplitude value of the first bioelectrical impedance information is less than the threshold.

For example, the determination module 2540h can pre-acquire and analyze bioelectrical impedance information of the inner side of the limb and bioelectrical impedance information of the outer side of the limb, suppose that an average amplitude value of the bioelectrical impedance information of the inner side falls within a first interval ($I_{min}$, $I_{max}$) and suppose that an average amplitude value of the bioelectrical impedance information of the outer side falls within a second interval ($O_{min}$, $O_{max}$), $I_{max} < O_{min}$, it can be determined that the threshold is M, and $I_{max} < M < O_{min}$. That is to say, the threshold M is a value between the first interval and the second interval.

Therefore, if an average amplitude value of the first bioelectrical impedance information is greater than the threshold M, the identification module 2520 considers that the average value falls within the second interval, and the first side is not the inner side of the limb, that is, is the outer side of the limb; if the average amplitude value of the first bioelectrical impedance information is less than the threshold M, it can be considered that the average value falls within the first interval, and the first side is the inner side of the limb.

Figure 40:
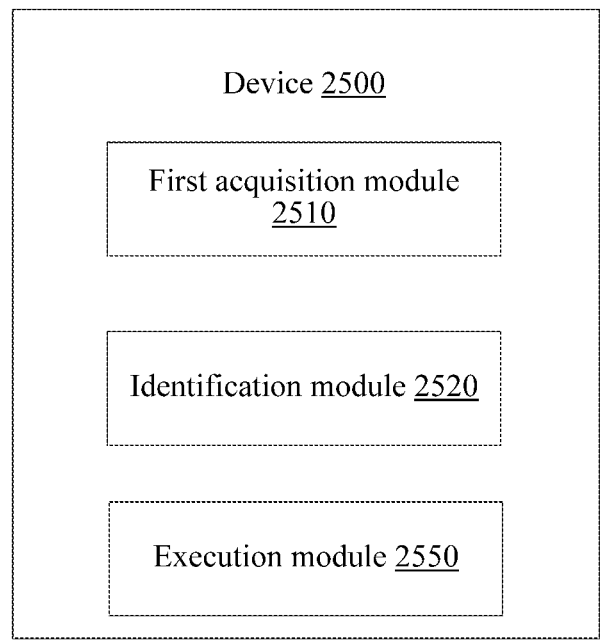
FIG. 40 is a modular structure diagram of a device for determining inner and outer sides of limbs according to an embodiment of the present application.

Referring to FIG. 40, in some embodiments, the device 2500 may further comprise:

an execution module 2550, configured to execute an operation according to an identification result.

For example, if it is displayed according to an identification result that the first side is the inner side of the limb, the execution module 2550 can control the device 2500 to continuously acquire somatosensory signals of the user at the first side; if it is displayed that the first side is not the inner side of the limb, the execution module 2550 can control the device 2500 to stop acquiring the somatosensory signals of the user at the first side but to acquire the somatosensory signals of the user at a second side opposite the first side.

Suppose that a smart watch that a user wears is provided with one group of somatosensory sensors respectively corresponding to the inner side and the outer side of the limb, the user does not need to consider the wearing manner when wearing the watch, and the smart watch will automatically stop contacting operation of the somatosensory sensors on the outer side of the limb but ensure contacting operation of the sensors on the inner side of the limb, thereby enhancing user experience.

Figure 41:
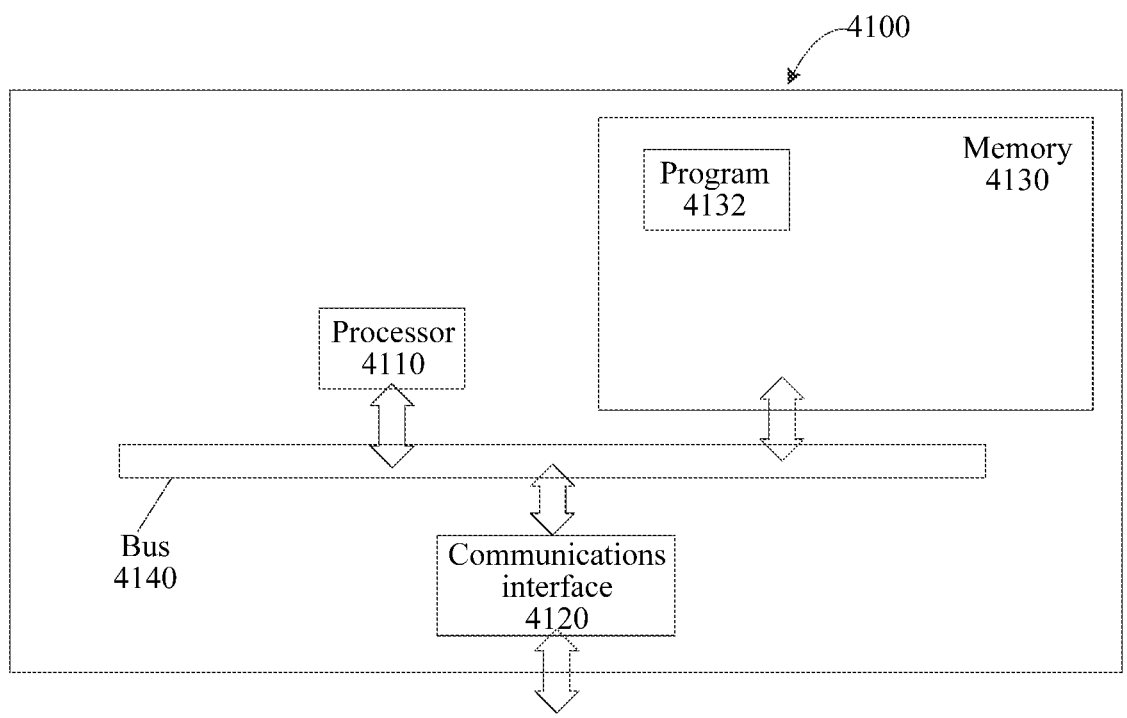
FIG. 41 is a schematic diagram of a device for determining inner and outer sides of limbs in some embodiments of the present application.

A hardware structure of the device for determining inner and outer sides of limbs according to another embodiment of the present application is as shown in FIG. 41. The specific embodiment of the present application does not limit specific implementation of the device for determining inner and outer sides of limbs; referring to FIG. 41, the device 4100 may comprise:

a processor 4110, a communications interface 4120, a memory 4130, and a communications bus 4140.

The processor 4110, the communications interface 4120, and the memory 4130 communicate with each other by using the communications bus 4140.

The communications interface 4120 is configured to communicate with other network elements.

The processor 4110 is configured to execute a program 4132, and specifically can implement relevant steps in the method embodiment shown in FIG. 1.

Specifically, the program 4132 may comprise a program code, where the program code comprises a computer operation instruction.

The processor 4110 may be a central processing unit (CPU), or an application specific integrated circuit (ASIC), or may be configured as one or more integrated circuits that implement the embodiments of the present application.

The memory 4130 is configured to store the program 4132. The memory 4130 may comprise a high speed random access memory (RAM), and may also comprise a non-volatile memory such as at least one magnetic disk storage. The program 4132 may specifically execute the following steps:

acquiring first somatosensory information of a first side of a limb of a user, the first side being an inner side or an outer side of the limb; and determining whether the first side is the inner side of the limb according to the first somatosensory information and reference information.

For the specific implementation of the steps in the program 4132, please refer to the corresponding descriptions of corresponding steps or modules in the foregoing embodiments, which are not described herein again. It may be clearly understood by a person skilled in the art that, for the purpose of convenient and brief description, reference may be made to the description of corresponding procedures in the foregoing method embodiments for detailed working procedures of the foregoing devices and modules, and details are not described herein again.

It can be appreciated by a person of ordinary skill in the art that, exemplary units and method steps described with reference to the embodiments disclosed herein can be implemented by electronic hardware or a combination of computer software and electronic hardware. Whether these functions are executed by hardware or software depends on specific applications and design constraints of the technical solution. A person skilled in the art may use different methods to implement the described functions for each specific application, but such implementation should not be construed as a departure from the scope of the present application.

If the function is implemented in the form of a software functional unit and is sold or used as an independent product, the product can be stored in a computer-readable storage medium. Based on this understanding, the technical solution of the present application essentially, or the part that makes contributions to the prior art, or a part of the technical solution may be embodied in the form of a software product; the computer software product is stored in a storage medium and comprises several instructions for enabling a computer device (which may be a personal computer, a controller, a network device, or the like) to execute all or some of the steps of the method in the embodiments of the present application. The foregoing storage medium comprises a USB flash disk, a removable hard disk, a read-only memory (ROM), a random access memory (RAM), a diskette, an optical disk or any other mediums that can store program codes.

The foregoing implementations are only used to describe the present application, but not to limit the present application. A person of ordinary skill in the art can still make various alterations and modifications without departing from the spirit and scope of the present application; therefore, all equivalent technical solutions also fall within the scope of the present application, and the patent protection scope of the present application should be defined by the claims.

What is claimed is:

1. A method for determining inner and outer sides of limbs implemented by a system comprising a processor, wherein the method comprises:

acquiring first somatosensory information of a first side of a limb of a user, the first side being an inner side or an outer side of the limb;

identifying whether the first side is the inner side of the limb according to the first somatosensory information and reference information, to generate an identification result, wherein the reference information is acquired at a second side opposite the first side on the limb; and executing an operation according to the identification result, wherein the executing an operation according to the identification result comprises:

automatically stopping acquiring of somatosensory information of the user at the second side, and continuously acquiring somatosensory information of the user at the first side in response to identifying that the first side is the inner side of the limb, wherein the first somatosensory information includes first body temperature information, wherein the method comprises:

acquiring the first body temperature information of the first side of the limb of the user; and determining whether the first side is the inner side of the limb according to the first body temperature information and the reference information, wherein the reference information includes second body temperature information acquired at the second side opposite the first side on the limb, and wherein the determining whether the first side is the inner side of the limb according to the first body temperature information and reference information comprises:

determining whether the first side is the inner side of the limb by comparing an average value of the first body temperature information and an average value of the second body temperature information.

2. The method of claim 1, wherein the determining whether the first side is the inner side of the limb by comparing an average value of the first body temperature information and an average value of the second body temperature information comprises:

determining that the first side is the inner side of the limb in response to determining that the average value of the first body temperature information is greater than the average value of the second body temperature information; and determining that the first side is not the inner side of the limb in response to determining that the average value of the first body temperature information is less than the average value of the second body temperature information.

3. The method of claim 1, wherein the reference information includes a threshold determined according to body temperature information of the inner side and body temperature information of the outer side of the limb.

4. The method of claim 3, wherein the determining whether the first side is the inner side of the limb according to the first body temperature information and reference information comprises:
determining that the first side is the inner side of the limb in response to determining that an average value of the first body temperature information is greater than the threshold; and
determining that the first side is not the inner side of the limb in response to determining that the average value of the first body temperature information is less than the threshold.

5. The method of claim 1, wherein the first somatosensory information includes first skin conductive information; and
the method comprises:
acquiring the first skin conductive information of the first side of the limb of the user; and
determining whether the first side is the inner side of the limb according to the first skin conductive information and the reference information.

6. The method of claim 5, wherein the reference information includes second skin conductive information acquired at the second side opposite the first side on the limb.

7. The method of claim 6, wherein the determining whether the first side is the inner side of the limb according to the first skin conductive information and reference information comprises:
determining whether the first side is the inner side of the limb by comparing an average value of the first skin conductive information and an average value of the second skin conductive information.

8. The method of claim 7, wherein the determining whether the first side is the inner side of the limb by comparing an average value of the first skin conductive information and an average value of the second skin conductive information comprises:
determining that the first side is the inner side of the limb in response to determining that the average value of the first skin conductive information is greater than the average value of the second skin conductive information; and
determining that the first side is not the inner side of the limb in response to determining that the average value of the first skin conductive information is less than the average value of the second skin conductive information.

9. The method of claim 5, wherein the reference information includes a threshold determined according to skin conductive information of the inner side and skin conductive information of the outer side of the limb.

10. The method of claim 9, wherein the determining whether the first side is the inner side of the limb according to the first skin conductive information and reference information comprises:
determining that the first side is the inner side of the limb in response to determining that an average value of the first skin conductive information is greater than the threshold; and
determining that the first side is not the inner side of the limb in response to determining that the average value of the first skin conductive information is less than the threshold.

11. The method of claim 1, wherein the first somatosensory information includes first PH information; and
the method comprises:
acquiring the first PH information of the first side of the limb of the user; and
determining whether the first side is the inner side of the limb according to the first PH information and the reference information.

12. The method of claim 11, wherein the reference information include second PH information acquired at the second side opposite the first side on the limb.

13. The method of claim 12, wherein the determining whether the first side is the inner side of the limb according to the first PH information and reference information comprises:
determining whether the first side is the inner side of the limb by comparing an average value of the first PH information and an average value of the second PH information.

14. The method of claim 13, wherein the determining whether the first side is the inner side of the limb by comparing an average value of the first PH information and an average value of the second PH information comprises:
determining that the first side is the inner side of the limb in response to determining that the average value of the first PH information is less than the average value of the second PH information; and
determining that the first side is not the inner side of the limb in response to determining that the average value of the first PH information is greater than the average value of the second PH information.

15. The method of claim 11, wherein the reference information is a threshold determined according to PH information of the inner side and PH information of the outer side of the limb.

16. The method of claim 15, wherein the determining whether the first side is the inner side of the limb according to the first PH information and reference information comprises:
determining that the first side is the inner side of the limb in response to determining that an average value of the first PH information is less than the threshold; and
determining that the first side is not the inner side of the limb in response to determining that the average value of the first PH information is greater than the threshold.

17. The method of claim 1, wherein the first somatosensory information is first photoplethysmograph (PPG) information; and
the method comprises:
acquiring the first PPG information of the first side of the limb of the user; and
determining whether the first side is the inner side of the limb according to the first PPG information and the reference information.

18. The method of claim 17, wherein the reference information include second PPG information acquired at the second side opposite the first side on the limb.

19. The method of claim 18, wherein the determining whether the first side is the inner side of the limb according to the first PPG information and reference information comprises:
determining whether the first side is the inner side of the limb by comparing an average amplitude value of the first PPG information and an average amplitude value of the second PPG information.

20. The method of claim 19, wherein the determining whether the first side is the inner side of the limb by comparing an average amplitude value of the first PPG information and an average amplitude value of the second PPG information comprises:
   determining that the first side is the inner side of the limb in response to determining that the average amplitude value of the first PPG information is greater than the average amplitude value of the second PPG information; and
   determining that the first side is not the inner side of the limb in response to determining that the average amplitude value of the first PPG information is less than the average amplitude value of the second PPG information.

21. The method of claim 17, wherein the reference information includes a threshold determined according to PPG information of the inner side and PPG information of the outer side of the limb.

22. The method of claim 21, wherein the determining whether the first side is the inner side of the limb according to the first PPG information and reference information comprises:
   determining that the first side is the inner side of the limb in response to determining that an average amplitude value of the first PPG information is greater than the threshold; and
   determining that the first side is not the inner side of the limb in response to determining that the average amplitude value of the first PPG information is less than the threshold.

23. The method of claim 1, wherein the first somatosensory information includes first blood oxygen information; and
   the method comprises:
   acquiring the first blood oxygen information of the first side of the limb of the user; and
   determining whether the first side is the inner side of the limb according to the first blood oxygen information and the reference information.

24. The method of claim 23, wherein the reference information includes second blood oxygen information acquired at the second side opposite the first side on the limb.

25. The method of claim 24, wherein the determining whether the first side is the inner side of the limb according to the first blood oxygen information and reference information comprises:
   determining whether the first side is the inner side of the limb by comparing an average value of the first blood oxygen information and an average value of the second blood oxygen information.

26. The method of claim 25, wherein the determining whether the first side is the inner side of the limb by comparing an average value of the first blood oxygen information and an average value of the second blood oxygen information comprises:
   determining that the first side is the inner side of the limb in response to determining that the average value of the first blood oxygen information is greater than the average value of the second blood oxygen information; and
   determining that the first side is not the inner side of the limb in response to determining that the average value of the first blood oxygen information is less than the average value of the second blood oxygen information.

27. The method of claim 23, wherein the reference information includes a threshold determined according to blood oxygen information of the inner side and blood oxygen information of the outer side of the limb.

28. The method of claim 27, wherein the determining whether the first side is the inner side of the limb according to the first blood oxygen information and reference information comprises:
   determining that the first side is the inner side of the limb in response to determining that an average value of the first blood oxygen information is greater than the threshold; and
   determining that the first side is not the inner side of the limb in response to determining that the average value of the first blood oxygen information is less than the threshold.

29. The method of claim 1, wherein the first somatosensory information includes first fat information; and
   the method comprises:
   acquiring the first fat information of the first side of the limb of the user; and
   determining whether the first side is the inner side of the limb according to the first fat information and the reference information.

30. The method of claim 29, wherein the reference information includes second fat information acquired at the second side opposite the first side on the limb.

31. The method of claim 30, wherein the determining whether the first side is the inner side of the limb according to the first fat information and reference information comprises:
   determining whether the first side is the inner side of the limb by comparing an average value of the first fat information and an average value of the second fat information.

32. The method of claim 31, wherein the determining whether the first side is the inner side of the limb by comparing an average value of the first fat information and an average value of the second fat information comprises:
   determining that the first side is the inner side of the limb in response to determining that the average value of the first fat information is less than the average value of the second fat information; and
   determining that the first side is not the inner side of the limb in response to determining that the average value of the first fat information is greater than the average value of the second fat information.

33. The method of claim 29, wherein the reference information includes a threshold determined according to fat information of the inner side and fat information of the outer side of the limb.

34. The method of claim 33, wherein the determining whether the first side is the inner side of the limb according to the first fat information and reference information comprises:
   determining that the first side is the inner side of the limb in response determining to that an average value of the first fat information is less than the threshold; and
   determining that the first side is not the inner side of the limb in response to determining that the average value of the first fat information is greater than the threshold.

35. The method of claim 1, wherein the first somatosensory information includes first humidity information; and
   the method comprises:

acquiring the first humidity information of the first side of the limb of the user; and determining whether the first side is the inner side of the limb according to the first humidity information and the reference information.

36. The method of claim 35, wherein the reference information includes second humidity information acquired at the second side opposite the first side on the limb.

37. The method of claim 36, wherein the determining whether the first side is the inner side of the limb according to the first humidity information and reference information comprises:

determining whether the first side is the inner side of the limb by comparing an average value of the first humidity information and an average value of the second humidity information.

38. The method of claim 37, wherein the determining whether the first side is the inner side of the limb by comparing an average value of the first humidity information and an average value of the second humidity information comprises:

determining that the first side is the inner side of the limb in response to determining that the average value of the first humidity information is greater than the average value of the second humidity information; and determining that the first side is not the inner side of the limb in response to determining that the average value of the first humidity information is less than the average value of the second humidity information.

39. The method of claim 35, wherein the reference information includes a threshold determined according to humidity information of the inner side and humidity information of the outer side of the limb.

40. The method of claim 39, wherein the determining whether the first side is the inner side of the limb according to the first humidity information and reference information comprises:

determining that the first side is the inner side of the limb in response to determining that an average value of the first humidity information is greater than the threshold; and determining that the first side is not the inner side of the limb in response to determining that the average value of the first humidity information is less than the threshold.

41. The method of claim 1, wherein the first somatosensory information includes first bioelectrical impedance information; and the method comprises:

acquiring the first bioelectrical impedance information of the first side of the limb of the user; and determining whether the first side is the inner side of the limb according to the first bioelectrical impedance information and the reference information.

42. The method of claim 41, wherein the method further comprises:

acquiring second bioelectrical impedance information at the second side opposite the first side on the limb as the reference information.

43. The method of claim 42, wherein the determining whether the first side is the inner side of the limb according to the first bioelectrical impedance information and reference information comprises:

determining whether the first side is the inner side of the limb by comparing an average amplitude value of the first bioelectrical impedance information and an average amplitude value of the second bioelectrical impedance information.

44. The method of claim 43, wherein the determining whether the first side is the inner side of the limb by comparing an average amplitude value of the first bioelectrical impedance information and an average amplitude value of the second bioelectrical impedance information comprises:

determining that the first side is not the inner side of the limb in response to determining that the average amplitude value of the first bioelectrical impedance information is greater than the average amplitude value of the second bioelectrical impedance information; and determining that the first side is the inner side of the limb in response to determining that the average amplitude value of the first bioelectrical impedance information is less than the average amplitude value of the second bioelectrical impedance information.

45. The method of claim 41, wherein the reference information is a threshold determined according to bioelectrical impedance information of the inner side and bioelectrical impedance information of the outer side of the limb.

46. The method of claim 45, wherein the determining whether the first side is the inner side of the limb according to the first bioelectrical impedance information and reference information comprises:

determining that the first side is not the inner side of the limb in response to determining that an average amplitude value of the first bioelectrical impedance information is greater than the threshold; and determining that the first side is the inner side of the limb in response to determining that the average amplitude value of the first bioelectrical impedance information is less than the threshold.

47. A device for determining inner and outer sides of limbs, wherein the device comprises a processor, coupled to a memory, that executes or facilitates execution of executable modules, the executable modules comprising:

a first acquisition module, configured to acquire first somatosensory information of a first side of a limb of a user, the first side being an inner side or an outer side of the limb;

an identification module, configured to identify whether the first side is the inner side of the limb according to the first somatosensory information and reference information, to generate an identification result, wherein the reference information is acquired at a second side opposite the first side on the limb; and an execution module, configured to execute an operation according to the identification result, wherein the execution module is configured to continuously acquire somatosensory information of the user at the first side in response to identifying that the first side is the inner side of the limb, wherein the first somatosensory information includes first body temperature information, wherein the first acquisition module is configured to acquire the first body temperature information of the first side of the limb of the user, wherein the identification module is configured to identify whether the first side is the inner side of the limb according to the first body temperature information and the reference information, wherein the executable modules further comprise:

a second acquisition module, configured to acquire second body temperature information at the second side opposite the first side on the limb as the reference information, and wherein the identification module is configured to identify whether the first side is the inner side of the limb by comparing an average value of the first body temperature information and an average value of the second body temperature information.

48. The device of claim 47, wherein the identification module is configured to identify that the first side is the inner side of the limb in response to determining that the average value of the first body temperature information is greater than the average value of the second body temperature information; and
to identify that the first side is not the inner side of the limb in response to determining that the average value of the first body temperature information is less than the average value of the second body temperature information.

49. The device of claim 47, wherein the executable modules further comprise:
a determination module, configured to determine a threshold according to body temperature information of the inner side and body temperature information of the outer side of the limb as the reference information.

50. The device of claim 49, wherein the identification module is configured to identify that the first side is the inner side of the limb in response to determining that an average value of the first body temperature information is greater than the threshold; and to identify that the first side is not the inner side of the limb in response to determining that the average value of the first body temperature information is less than the threshold.

51. The device of claim 47, wherein the first somatosensory information includes first skin conductive information;
wherein the first acquisition module is configured to acquire the first skin conductive information of the first side of the limb of the user; and
wherein the identification module is configured to identify whether the first side is the inner side of the limb according to the first skin conductive information and the reference information.

52. The device of claim 51, wherein the executable modules further comprise:
a second acquisition module, configured to acquire second skin conductive information at the second side opposite the first side on the limb as the reference information.

53. The device of claim 52, wherein the identification module is configured to identify whether the first side is the inner side of the limb by comparing an average value of the first skin conductive information and an average value of the second skin conductive information.

54. The device of claim 53, wherein the identification module is configured to identify that the first side is the inner side of the limb in response to determining that the average value of the first skin conductive information is greater than the average value of the second skin conductive information; and
to identify that the first side is not the inner side of the limb in response to determining that the average value of the first skin conductive information is less than the average value of the second skin conductive information.

55. The device of claim 51, wherein the executable modules further comprise:
a determination module, configured to determine a threshold according to skin conductive information of the inner side and skin conductive information of the outer side of the limb as the reference information.

56. The device of claim 55, wherein the identification module is configured to identify that the first side is the inner side of the limb in response to determining that an average value of the first skin conductive information is greater than the threshold; and
to identify that the first side is not the inner side of the limb in response to determining that the average value of the first skin conductive information is less than the threshold.

57. The device of claim 47, wherein the first somatosensory information includes first PH information;
wherein the first acquisition module is configured to acquire the first PH information of the first side of the limb of the user; and
wherein the identification module is configured to identify whether the first side is the inner side of the limb according to the first PH information and the reference information.

58. The device of claim 57, wherein the executable modules further comprise:
a second acquisition module configured to acquire second PH information at the second side opposite the first side on the limb as the reference information.

59. The device of claim 58, wherein the identification module is configured to identify whether the first side is the inner side of the limb by comparing an average value of the first PH information and an average value of the second PH information.

60. The device of claim 59, wherein the identification module is configured to identify that the first side is the inner side of the limb in response to determining that the average value of the first PH information is less than the average value of the second PH information; and
to identify that the first side is not the inner side of the limb in response to determining that the average value of the first PH information is greater than the average value of the second PH information.

61. The device of claim 57, wherein the executable modules further comprise:
a determination module, configured to determine a threshold according to PH information of the inner side and PH information of the outer side of the limb as the reference information.

62. The device of claim 61, wherein the identification module is configured to identify that the first side is the inner side of the limb in response to determining that an average value of the first PH information is less than the threshold; and
to identify that the first side is not the inner side of the limb in response to determining that the average value of the first PH information is greater than the threshold.

63. The device of claim 47, wherein the first somatosensory information includes first photoplethysmograph (PPG) information;
the first acquisition module is configured to acquire the first PPG information of the first side of the limb of the user; and
the identification module is configured to identify whether the first side is the inner side of the limb according to the first PPG information and the reference information.

64. The device of claim 63, wherein the executable modules further comprise:

a second acquisition module, configured to acquire second PPG information at the second side opposite the first side on the limb as the reference information.

65. The device of claim 64, wherein the identification module is configured to identify whether the first side is the inner side of the limb by comparing an average amplitude value of the first PPG information and an average amplitude value of the second PPG information.

66. The device of claim 65, wherein the identification module is configured to identify that the first side is the inner side of the limb in response to determining that the average amplitude value of the first PPG information is greater than the average amplitude value of the second PPG information; and
to identify that the first side is not the inner side of the limb in response to determining that the average amplitude value of the first PPG information is less than the average amplitude value of the second PPG information.

67. The device of claim 63, wherein the executable modules further comprise:
a determination module, configured to determine a threshold according to PPG information of the inner side and PPG information of the outer side of the limb as the reference information.

68. The device of claim 67, wherein the identification module is configured to identify that the first side is the inner side of the limb in response to determining that an average amplitude value of the first PPG information is greater than the threshold; and
to identify that the first side is not the inner side of the limb in response to determining that the average amplitude value of the first PPG information is less than the threshold.

69. The device of claim 47, wherein the first somatosensory information includes first blood oxygen information;
wherein the first acquisition module is configured to acquire the first blood oxygen information of the first side of the limb of the user; and
wherein the identification module is configured to identify whether the first side is the inner side of the limb according to the first blood oxygen information and the reference information.

70. The device of claim 69, wherein the executable modules further comprise:
a second acquisition module, configured to acquire second blood oxygen information at the second side opposite the first side on the limb as the reference information.

71. The device of claim 70, wherein the identification module is configured to identify whether the first side is the inner side of the limb by comparing an average value of the first blood oxygen information and an average value of the second blood oxygen information.

72. The device of claim 71, wherein the identification module is configured to identify that the first side is the inner side of the limb in response to determining that the average value of the first blood oxygen information is greater than the average value of the second blood oxygen information; and
to identify that the first side is not the inner side of the limb in response to determining that the average value of the first blood oxygen information is less than the average value of the second blood oxygen information.

73. The device of claim 69, wherein the executable modules further comprise:

a determination module, configured to determine a threshold according to blood oxygen information of the inner side and blood oxygen information of the outer side of the limb as the reference information.

74. The device of claim 73, wherein the identification module is configured to identify that the first side is the inner side of the limb in response to determining that an average value of the first blood oxygen information is greater than the threshold; and
to identify that the first side is not the inner side of the limb in response to determining that the average value of the first blood oxygen information is less than the threshold.

75. The device of claim 47, wherein the first somatosensory information is first fat information;
the first acquisition module is configured to acquire the first fat information of the first side of the limb of the user; and
the identification module is configured to identify whether the first side is the inner side of the limb according to the first fat information and the reference information.

76. The device of claim 75, wherein the executable modules further comprise:
a second acquisition module, configured to acquire second fat information at the second side opposite the first side on the limb as the reference information.

77. The device of claim 76, wherein the identification module is configured to identify whether the first side is the inner side of the limb by comparing an average value of the first fat information and an average value of the second fat information.

78. The device of claim 77, wherein the identification module is configured to identify that the first side is the inner side of the limb in response to determining that the average value of the first fat information is less than the average value of the second fat information; and
to identify that the first side is not the inner side of the limb in response to determining that the average value of the first fat information is greater than the average value of the second fat information.

79. The device of claim 75, wherein the executable modules further comprise:
a determination module, configured to determine a threshold according to fat information of the inner side and fat information of the outer side of the limb as the reference information.

80. The device of claim 79, wherein the identification module is configured to identify that the first side is the inner side of the limb in response to determining that an average value of the first fat information is less than the threshold; and
to identify that the first side is not the inner side of the limb in response to determining that the average value of the first fat information is greater than the threshold.

81. The device of claim 47, wherein the first somatosensory information is first humidity information;
the first acquisition module is configured to acquire the first humidity information of the first side of the limb of the user; and
the identification module is configured to identify whether the first side is the inner side of the limb according to the first humidity information and the reference information.

82. The device of claim 81, wherein the executable modules further comprise:

a second acquisition module, configured to acquire second humidity information at the second side opposite the first side on the limb as the reference information.

83. The device of claim 82, wherein the identification module is configured to identify whether the first side is the inner side of the limb by comparing an average value of the first humidity information and an average value of the second humidity information.

84. The device of claim 83, wherein the identification module is configured to identify that the first side is the inner side of the limb in response to determining that the average value of the first humidity information is greater than the average value of the second humidity information; and
identify that the first side is not the inner side of the limb in response to determining that the average value of the first humidity information is less than the average value of the second humidity information.

85. The device of claim 81, wherein the executable modules further comprise:
a determination module, configured to determine a threshold according to humidity information of the inner side and humidity information of the outer side of the limb as the reference information.

86. The device of claim 85, wherein the identification module is configured to identify that the first side is the inner side of the limb in response to determining that an average value of the first humidity information is greater than the threshold; and
to identify that the first side is not the inner side of the limb in response to determining that the average value of the first humidity information is less than the threshold.

87. The device of claim 47, wherein the first somatosensory information includes first bioelectrical impedance information;
wherein the first acquisition module is configured to acquire the first bioelectrical impedance information of the first side of the limb of the user; and
wherein the identification module is configured to identify whether the first side is the inner side of the limb according to the first bioelectrical impedance information and the reference information.

88. The device of claim 87, wherein the executable modules further comprise:
a second acquisition module, configured to acquire second bioelectrical impedance information at the second side opposite the first side on the limb as the reference information.

89. The device of claim 88, wherein the identification module is configured to determine whether the first side is the inner side of the limb by comparing an average amplitude value of the first bioelectrical impedance information and an average amplitude value of the second bioelectrical impedance information.

90. The device of claim 89, wherein the identification module is configured to determine that the first side is not the inner side of the limb in response to determining that the average amplitude value of the first bioelectrical impedance information is greater than the average amplitude value of the second bioelectrical impedance information; and
to determine that the first side is the inner side of the limb in response to determining that the average amplitude value of the first bioelectrical impedance information is less than the average amplitude value of the second bioelectrical impedance information.

91. The device of claim 87, wherein the executable modules further comprise:

a determination module, configured to determine a threshold according to bioelectrical impedance information of the inner side and bioelectrical impedance information of the outer side of the limb as the reference information.

92. The device of claim 91, wherein the identification module is configured to determine that the first side is not the inner side of the limb in response to determining that an average amplitude value of the first bioelectrical impedance information is greater than the threshold; and
to determine that the first side is the inner side of the limb in response to determining that the average amplitude value of the first bioelectrical impedance information is less than the threshold.

93. A wearable device, wherein the wearable device comprises the device for determining inner and outer sides of limbs of claim 47.

94. A non-transitory computer readable storage medium that stores at least one executable instruction, which, when executed by an apparatus, causes the apparatus to perform a method for determining inner and outer sides of limbs, the method comprising:
acquiring first somatosensory information of a first side of a limb of a user, the first side being an inner side or an outer side of the limb;
identifying whether the first side is the inner side of the limb according to the first somatosensory information and reference information, to generate an identification result, wherein the reference information is acquired at a second side opposite the first side on the limb; and
executing an operation according to the identification result,
wherein the executing an operation according to the identification result comprises:
automatically stopping acquiring of somatosensory information of the user at the second side, and continuously acquiring somatosensory information of the user at the first side in response to identifying that the first side is the inner side of the limb, wherein the first somatosensory information includes first body temperature information, wherein the method comprises:
acquiring the first body temperature information of the first side of the limb of the user; and
determining whether the first side is the inner side of the limb according to the first body temperature information and the reference information,
wherein the reference information includes second body temperature information acquired at the second side opposite the first side on the limb, and
wherein the determining whether the first side is the inner side of the limb according to the first body temperature information and reference information comprises:
determining whether the first side is the inner side of the limb by comparing an average value of the first body temperature information and an average value of the second body temperature information.

95. A device for determining inner and outer sides of limbs, characterized by comprising a processor and a memory, the memory storing computer executable instructions, the processor being connected to the memory through a communication bus, and when the device for determining inner and outer sides of limbs operates, the processor executing the computer executable instructions stored in the memory, so that the device for determining inner and outer sides of limbs executes operations, comprising:

acquiring first somatosensory information of a first side of a limb of a user, the first side being an inner side or an outer side of the limb;

identifying whether the first side is the inner side of the limb according to the first somatosensory information and reference information, to generate an identification result, wherein the reference information is acquired at a second side opposite the first side on the limb; and executing an operation according to the identification result, wherein the executing an operation according to the identification result comprises:

automatically stopping acquiring of somatosensory information of the user at the second side, and continuously acquiring somatosensory information of the user at the first side in response to identifying that the first side is the inner side of the limb, wherein the first somatosensory information includes first body temperature information, wherein the operations further comprise:

acquiring the first body temperature information of the first side of the limb of the user; and determining whether the first side is the inner side of the limb according to the first body temperature information and the reference information, wherein the reference information includes second body temperature information acquired at the second side opposite the first side on the limb, and wherein the determining whether the first side is the inner side of the limb according to the first body temperature information and reference information comprises:

determining whether the first side is the inner side of the limb by comparing an average value of the first body temperature information and an average value of the second body temperature information.

* * * * *